(12) United States Patent
Stillwell et al.

(10) Patent No.: US 12,004,843 B2
(45) Date of Patent: Jun. 11, 2024

(54) FREQUENCY DOMAIN DIFFUSE OPTICAL SPECTROSCOPY DEVICE AND OPTICAL DETECTOR CALIBRATION METHOD

(71) Applicant: UNIVERSITY OF NOTRE DAME DU LAC, Notre Dame, IN (US)

(72) Inventors: Roy A. Stillwell, Notre Dame, IN (US); Vincent James Kitsmiller, Notre Dame, IN (US); Thomas D. O'Sullivan, Notre Dame, IN (US)

(73) Assignee: UNIVERSITY OF NOTRE DAME DU LAC, Notre Dame, IN (US)

(*) Notice: Subject to any disclaimer, the term of this patent is extended or adjusted under 35 U.S.C. 154(b) by 877 days.

(21) Appl. No.: 17/045,070

(22) PCT Filed: Apr. 5, 2019

(86) PCT No.: PCT/US2019/026088
§ 371 (c)(1),
(2) Date: Oct. 2, 2020

(87) PCT Pub. No.: WO2019/195749
PCT Pub. Date: Oct. 10, 2019

(65) Prior Publication Data
US 2021/0161389 A1 Jun. 3, 2021

Related U.S. Application Data

(60) Provisional application No. 62/653,364, filed on Apr. 5, 2018.

(51) Int. Cl.
*A61B 5/00* (2006.01)
(52) U.S. Cl.
CPC .......... *A61B 5/0075* (2013.01); *A61B 5/0013* (2013.01); *A61B 5/7228* (2013.01);
(Continued)

(58) Field of Classification Search
CPC .... A61B 5/0075; A61B 5/0013; A61B 5/7228
See application file for complete search history.

(56) References Cited

U.S. PATENT DOCUMENTS 8,244,332 B2  8/2012 Azar et al.
8,320,996 B2  11/2012 Panasyuk et al.
(Continued)

FOREIGN PATENT DOCUMENTS

EP  3773204 B1  7/2023

OTHER PUBLICATIONS

"Frequency domain near-infrared multiwavelength imager design using high-speed, direct analog-to-digital conversion" by B.B. Zimmermann et al. J Biomed Optics. 21(1). 016010 1-8. (Year: 2016).*

(Continued)

*Primary Examiner* — Jason M Ip
(74) *Attorney, Agent, or Firm* — Cognition IP, P.C.; Edward Steakley

(57) ABSTRACT

A frequency domain diffuse optical spectroscopy (FD-DOS) device and calibration method. The FD-DOS device includes a radio frequency signal generator, a driver, a light source, a silicon photomultiplier, an analog to digital conversion circuit, and an electronic processing circuit. The light source is configured to generate modulated light at a plurality of different wavelengths and modulation frequencies. The silicon photomultiplier is configured to generate analog detection signals indicative of detected optical signals. The analog to digital conversion circuit is configured to generate digital sample values from the analog detection signals. The electronic processing circuit is configured to determine absorption values and scattering values based on the digital sample values. The electronic processing circuit is also configured to determine concentration values based (Continued)

on the absorption values and the scattering values. The electronic processing circuit is further configured to determine an image stream based on the concentration values.

19 Claims, 18 Drawing Sheets

(52) U.S. Cl.
CPC ...... *A61B 5/742* (2013.01); *A61B 2560/0214* (2013.01); *A61B 2560/0223* (2013.01)

(56) References Cited

U.S. PATENT DOCUMENTS

| | | | |
|---|---|---|---|
| 8,649,849 | B2 | 2/2014 | Liu et al. |
| 9,772,280 | B2 | 9/2017 | Cerussi et al. |
| 9,820,655 | B2 | 11/2017 | Ramanujam et al. |
| 9,861,319 | B2 | 1/2018 | Yu et al. |
| 10,653,346 | B2 * | 5/2020 | Zarandi ............... A61B 5/7278 |
| 2002/0033454 | A1 | 3/2002 | Cheng et al. |
| 2004/0247021 | A1 | 12/2004 | Ishioka et al. |
| 2008/0009748 | A1 | 1/2008 | Gratton et al. |
| 2009/0117606 | A1 | 5/2009 | Tunnell et al. |
| 2009/0234225 | A1 | 9/2009 | Martin et al. |
| 2013/0289381 | A1 | 10/2013 | Oraevsky et al. |
| 2015/0165234 | A1 | 6/2015 | Bharat et al. |
| 2015/0351635 | A1 | 12/2015 | Cerussi et al. |
| 2016/0070830 | A1 | 3/2016 | Moroz et al. |
| 2016/0235372 | A1 | 8/2016 | Schneider et al. |
| 2016/0317035 | A1 | 11/2016 | Hendriks et al. |
| 2016/0345858 | A1 | 12/2016 | Tromberg et al. |
| 2016/0361017 | A1 | 12/2016 | Busch, Jr. et al. |
| 2017/0003316 | A1 | 1/2017 | Yang et al. |
| 2017/0209083 | A1 * | 7/2017 | Zarandi ............... A61B 5/0816 |
| 2017/0235134 | A1 | 8/2017 | Border et al. |
| 2017/0354359 | A1 | 12/2017 | Belthangady et al. |
| 2018/0110458 | A1 | 4/2018 | Barbour et al. |
| 2018/0134802 | A1 | 5/2018 | Mukherjee |
| 2018/0303391 | A1 | 10/2018 | Roblyer et al. |

OTHER PUBLICATIONS

"Photomultiplier Tubes" Basics and Applications 4th Ed. (Year: 2017).*
"A wireless handheld probe with spectrally constrained evolution strategies for diffuse optical imaging of tissue" by M.L. Flexman et al. Review of Scientific Instruments. 83, 033108. (Year: 2012).*
Mora AD, Martinenghi E, Contini D, Tosi A, Boso G, Durduran T, Arridge S, Martelli F, Farina A, Torricelli A, Pifferi A. Fast silicon photomultiplier improves signal harvesting and reduces complexity in time-domain diffuse optics. Opt Express. Jun. 1, 2015;23(11):13937-46. doi: 10.1364/OE.23.013937.
Applegate MB, Roblyer D. Multi-distance diffuse optical spectroscopy with a single optode via hypotrochoidal scanning. Opt Lett. Feb. 15, 2018;43(4):747-750. doi: 10.1364/OL.43.000747.
Extended European search report received in European application No. 23187363.9, dated Aug. 4, 2023.
Beck et al., "Finite-precision goertzel filters used for signal tone detection", IEEE Trans. Circuits Syst. II Analog Digit. Signal Process, 48(7), 2001, pp. 691-700.
Bevilacqua et al., "In vivo local determination of tissue optical properties: Applications to human brain", Appl. Opt., 38 (22), 1999, p. 4939.
Boyd et al., "Heritability of mammographic density, a risk factor for breast cancer". N Engl J Med, vol. 347, 2002, pp. 886-894.
Buzhan et al., "Silicon photomultiplier and its possible applications", Nuclear Instruments and Methods in Physics Research Section A: Accelerators, Spectrometers, Detectors and Associated Equipment, vol. 504, Issues 1-3, May 2003, pp. 48-52.
Cates et al., "Highly multiplexed signal readout for a time-of-flight positron emission tomography detector based on silicon photomultipliers", J. of Medical Imaging, vol. 4, No. 1, 2017, pp. 011012-1-9.
Cerussi et al., "Quality control and assurance for validation of DOS/I measurements," Proceedings SPIE: Design and Performance Validation of Phantoms Used in Conjunction with Optical Measurement of Tissue II, 2010, 7567.
Cerussi et al., "Diffuse optical spectroscopic imaging correlates with final pathological response in breast cancer neoadjuvant chemotherapy", Phil. Trans. R. Soc. A, vol. 369, 2011, pp. 4512-4530.
Cerussi et al., "Noninvasive monitoring of red blood cell transfusion in very low birthweight infants using diffuse optical spectroscopy," J Biomed Opt, 10(5), 2005, p. 51401.
Cerussi et al., "Tissue phantoms in multicenter clinical trials for diffuse optical technologies," Biomedical Optics Express, vol. 3, No. 5, 2012, pp. 966-971.
Chance et al., "Phase measurement of light absorption and scatter in human tissue," Rev. Sci. Instrum., 69(10), 1998, p. 3457.
Di Sieno et al., "Time-domain diffuse optical tomography using silicon photomultipliers: feasibility study", J. of Biomedical Optics, vol. 21, No. 11, 2016, pp. 116002-1-9.
Dolgoshein et al., "Status report on silicon photomultiplier development and its applications", Nuclear Instruments and Methods in Physics Research Section A: Accelerators, Spectrometers, Detectors and Associated Equipment, vol. 563, Issue 2, Jul. 2006, pp. 368-376.
Eggebrecht et al., "Mapping distributed brain function and networks with diffuse optical tomography", Nature Photonics. vol. 8, 2014, pp. 448-454.
Fishkin et al., "Frequency-domain photon migration measurements of normal and malignant tissue optical properties in a human subject", Applied Optics, vol. 36, No. 1, 1997, pp. 10-20.
Fishkin et al., "Gigahertz photon density waves in a turbid medium: Theory and experiments," Phys. Rev. E, vol. 53, No. 3, 1996, pp. 2307-2319.
Ganesan et al., "Effect of Blood Flow Restriction on Tissue Oxygenation during Knee Extension NIH Public Access", Med Sci Sport. Exerc., 47(1), 2015, pp. 185-193.
Haskell et al., "Boundary conditions for the diffusion equation in radiative transfer", J. Opt. Soc. Am. A, vol. 11, No. 10, 1994, pp. 2727-2741.
International Search Report and Written Opinion for Application No. PCT/US19/26088 dated Aug. 9, 2019 (15 pages).
Jung et al., "Note: A simple broad bandwidth undersampling frequency-domain digital diffuse optical spectroscopy system", Rev. Sci. Instrum., 85(7), 2014, pp. 4-6.
Kim et al., "US-guided diffuse optical tomography for breast lesions: the reliability of clinical experience", European Radiology, 2011, vol. 21, No. 7, 7 pages.
Kitsmiller et al., "Next generation frequency domain diffuse optical imaging systems using silicon photomultipliers", Opt. Lett., vol. 44, No. 3, 2019, pp. 562-565.
Kwon et al., "Reaching 200-ps timing resolution in a time-of-flight and depth-of-interaction positron emission tomography detector using phosphor-coated crystals and high-density silicon photomultipliers", J. of Medical Imaging, vol. 3, No. 4, 2016, pp. 043501.
Leproux et al., "Differential diagnosis of breast masses in South Korean premenopausal women using diffuse optical spectroscopic imaging," J. Biomed. Opt., vol. 21, No. 7, 2016, p. 074001.
Meng et al., "Impact of phenylephrine administration on cerebral tissue oxygen saturation and blood volume is modulated by carbon dioxide in anaesthetized patients", British Journal of Anaesthesia, vol. 108, No. 5, 2012, pp. 815-822.
Mora et al., "Fast silicon photomultiplier improves signal harvesting and reduces complexity in time-domain diffuse optics", Optics Express, vol. 23, No. 11, 2015, pp. 13937-13946.
No et al., "Design and testing of a miniature broadband frequency domain photon migration instrument", Journal of Biomedical Optics, vol. 13, No. 5., 2008, pp. 050509-1-3.
O'Sullivan et al., "Diffuse optical imaging using spatially and temporally modulated light", J. Biomed. Opt., vol. 17, No. 7, 2012, p. 0713111.
O'Sullivan et al., "Optical imaging correlates with magnetic resonance imaging breast density and reveals composition changes during neoadjuvant chemotherapy", Breast Cancer Research, 2013, 15 pages.

(56) References Cited

OTHER PUBLICATIONS

Pham et al., "Noninvasive monitoring of hemodynamic stress using quantitative near-infrared frequency-domain photon migration spectroscopy", J. Biomed. Opt., 7(1), 2002, p. 34.

Pham et al., "Broad bandwidth frequency domain instrument for quantitative tissue optical spectroscopy", Rev. Sci. Instrum., 71(6), 2000, pp. 83-100.

Puszka et al., "Time-resolved diffuse optical tomography using fast-gated single photon avalance diodes", Biomedical Optics Express, vol. 4, No. 8, 2013, pp. 1351-1365.

Re et al., "Probe-hosted silicon photomultipliers for time-domain functional near-infrared spectroscopy: phantom and in vivo tests", Neurophotonics, vol. 3, No. 4, 2016, p. 045004.

Renker, "New trends on photodectors", Nuclear Instruments and Methods in Physics Research Section A: Accelerators, Spectrometers, Detectors and Associated Equipment, vol. 571, Issue 1-2, Feb. 2007, pp. 1-6.

Roblyer et al., "Feasibility of Direct Digital Sampling for Diffuse Optical Frequency Domain Spectroscopy in Tissue", Meas Sci Technol., Apr. 2013, vol. 24, No. 4, pp. 04550.

Shokoufi et al., "Novel Handheld Diffuse Optical Spectroscopy Probe for Breast Cancer Assessment: Clinical Study", J. of Biomed Sci, 2017, vol. 6, No. 5, 6 pages.

Svaasand et al., "Properties of optical waves in turbid media", Future Trends in Biomedical Applications of Lasers, vol. 1525, 1991, pp. 41-51.

Sysel et al., "Goertzel algorithm generalized to non-integer multiples of fundamental frequency", Eurasip J. Adv. Signal Process, 56, 2012, 8 pages.

Tanamai et al., "Diffuse optical spectroscopy measurements of healing in breast tissue after core biopsy: case study," Journal of Biomedical Optics, 2009, vol. 14, No. 1, pp. 014024-1-9.

Taroni et al., "Optical identification of subjects at high risk for developing breast cancer", J. of Biomedical Optics, vol. 18, No. 6, 2013, pp. 060507-1-3.

Torjesen et al., "Ultrafast wavelength multiplexed broad bandwidth digital diffuse optical spectroscopy for in vivo extraction of tissue optical properties", J. Biomed. Opt., 2017, vol. 22, No. 3, p. 036009.

Tromberg et al., "Non-invasive measurements of breast tissue optical properties using frequencydomain photon migration", Phil. Trans. R. Soc. Lond., 1997, 352, pp. 661-668.

Tromberg et al., "Noninvasive in vivo characterization of breast tumors using photon migration spectroscopy", Neoplasia, 2(1-2), 2000, pp. 26-40.

Tromberg et al., "Predicting Responses to Neoadjuvant Chemotherapy in Breast Cancer: ACRIN 6691 Trial of Diffuse Optical Spectroscopic Imaging", Cancer Research 2016, 13 pages.

Ueda et al., "Baseline tumor oxygen saturation correlates with a pathologic complete response in breast cancer patients undergoing neoadjuvant chemotherapy", Cancer Res. Sep. 2012, vol. 72, No. 17, pp. 4318-4328.

Xu et al., "A prospective pilot clinical trial evaluating the utility of a dynamic near-infrared imaging device for characterizing suspicious breast lesions", Breast Cancer Research, 2007, vol. 9, No. 6, 12 pages.

Zhang et al., "A Wearable Goggle Navigation System for Dual-Mode Optical and Ultrasound Localization of Suspicious Lesions: Validation Studies Using Tissue-Simulating Phantoms and an Ex Vivo Human Breast Tissue Model", PLoS One, Jul. 2016, 13 pages.

Zhang et al., "Time-Correlated Raman and Fluorescence Spectroscopy Based on a Silicon Photomultiplier and Time-Correlated Single Photon Counting Technique", Applied Spectroscopy, vol. 67, No. 136, Feb. 2013, pp. 136-140.

Zhao et al., "Quantitative real-time pulse oximetry with ultrafast frequency-domain diffuse optics and deep neural network processing", Biomedical Optics Express, vol. 9, No. 12, 2018, pp. 12 pages..

Zimmerman et al., "Silicon photomultipliers for improved detection of low light levels in miniature near-infrared spectroscopy instruments", Biomedical Optics Express, vol. 4, No. 5, 2013, pp. 659-666.

Masters, "Book Review: Biomedical Photonics Handbook", Journal of Biomedical Optics, vol. 9, No. 5, 2004, pp. 1110-1111.

European Patent Office Partial Supplementary Search Report for Application No. 19781359.5 dated Jan. 11, 2022 (16 pages).

Mastanduno et al., "Automatic and robust calibration of optical detector arrays for biomedical diffuse optical spectroscopy", Biomedical Optics Express, 2012, vol. 3, No. 10, pp. 2339-2352.

Kitsmiller et al., "Optimizing sensitivity and dynamic range of silicon photomultipliers for frequency-domain near infrared spectroscopy", Biomedical Optics Express, 2020, vol. 11, No. 9, pp. 5373-5387.

* cited by examiner

FREQUENCY DOMAIN DIFFUSE OPTICAL SPECTROSCOPY DEVICE AND OPTICAL DETECTOR CALIBRATION METHOD

RELATED APPLICATIONS

This application is a U.S. national stage entry of International Patent Application No. PCT/US2019/026088, filed on Apr. 5, 2019, which claims priority to U.S. Provisional Patent Application No. 62/653,364, entitled "HANDHELD DIFFUSE OPTICAL SPECTROSCOPY DEVICE FOR BREAST CANCER RISK ASSESSMENT AND DIFFERENTIAL DIAGNOSIS," filed on Apr. 5, 2018, the entire contents of each of which are fully incorporated herein by reference.

BACKGROUND

Frequency domain diffuse optical spectroscopy (FD-DOS) is a non-invasive optical imaging technique for characterizing biological tissue. Current FD-DOS designs use Avalanche photodiodes (APDs) or photomultiplier tubes (PMTs) as optical detectors. However, supplying the high voltage bias needed for both APDs and PMTs requires the use of high-voltage modules with large footprints, which limits their practical use in portable FD-DOS systems. In addition, current FD-DOS designs are limited to scan the range of optical powers in which the optical detector has a linear response, which limits their dynamic range.

SUMMARY

A silicon photomultiplier (SiPM) provides equal or better performance in FD-DOS applications than an APD or a PMT, but operates at a lower voltage bias that can be supplied by a high-voltage module with a smaller footprint. Thus, the disclosure provides a frequency domain diffuse optical spectroscopy (FD-DOS) device that includes, in one embodiment, a radio frequency signal generator, a driver, a light source, a silicon photomultiplier, an analog to digital conversion circuit, and an electronic processing circuit. The driver is coupled to the radio frequency signal generator. The light source is coupled to the driver and is configured to generate modulated light at a plurality of different wavelengths and a plurality of different modulation frequencies. The light source is for emitting the modulated light at a sample. The silicon photomultiplier is configured to detect analog signals indicative of amplitude and phase of radio frequency modulation components of detected optical signals emanating from the sample in response to the modulated light. The analog to digital conversion circuit is coupled to the silicon photomultiplier and is configured to generate digital sample values from the analog detection signals. The electronic processing circuit is coupled to the analog to digital conversion circuit and is configured to determine absorption values and scattering values based on the digital sample values. The electronic processing circuit is also configured to determine concentration values based on the absorption values and the scattering values. The electronic processing circuit is further configured to determine an image stream based on the concentration values.

The disclosure also provides a method for calibrating an optical detector in a diffuse optical spectroscopy device. The method includes measuring a first sample with the optical detector to determine a measured power response. The method also includes determining an inverse response based on the measured power response and a predetermined power response of the first sample. The method further includes measuring a second sample with the optical detector to determine a first frequency response. The method also includes adjusting the first frequency response based on the inverse response to determine a second frequency response. The method further includes determining a third frequency response based on predetermined absorption and scattering coefficients of the second sample. The method further includes determining a plurality of correction factors based on the second frequency response and the third frequency response.

Other aspects of the invention will become apparent by consideration of the detailed description and accompanying drawings.

DETAILED DESCRIPTION

Figure 1:
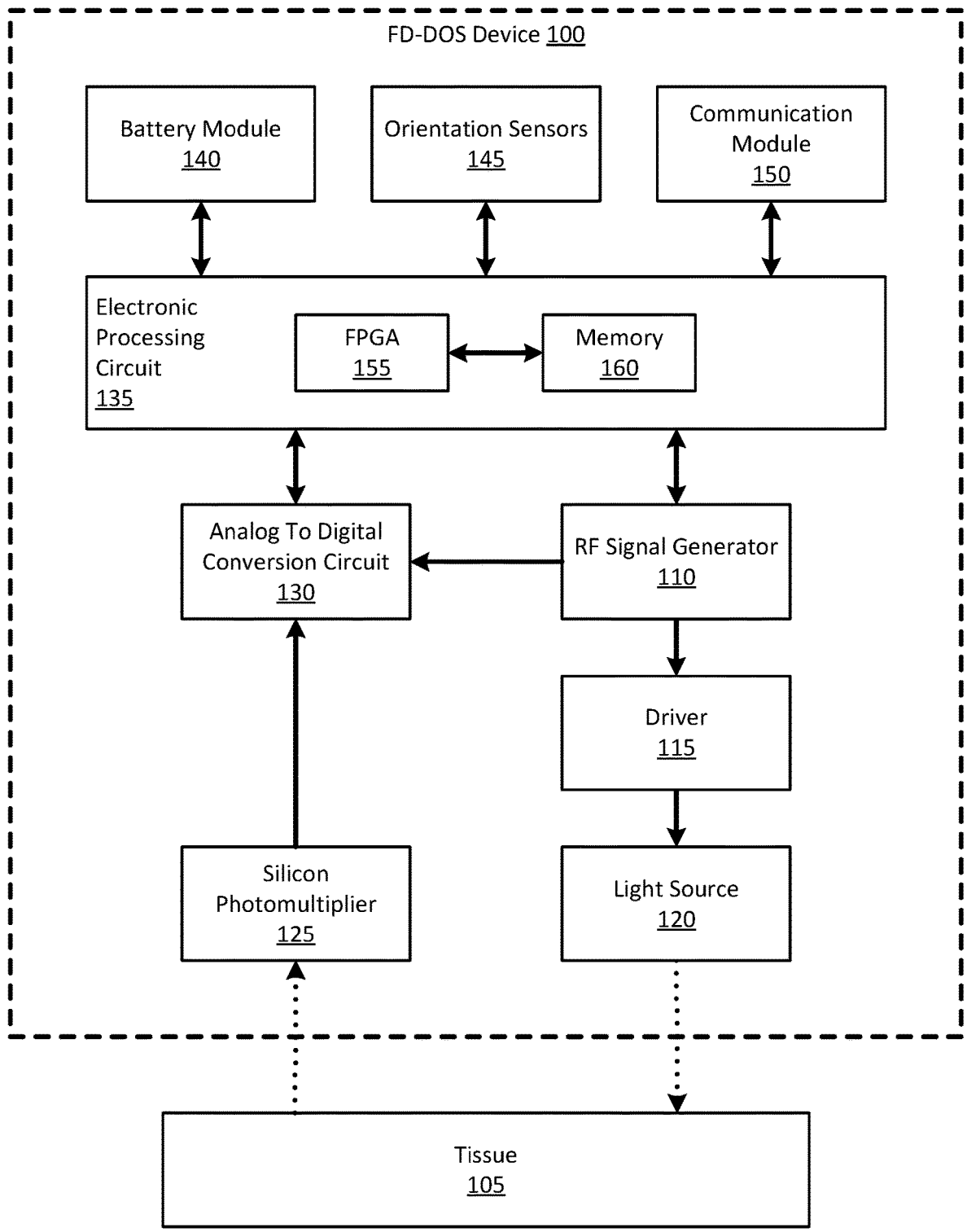
FIG. 1 is a diagram of a frequency domain diffuse optical spectroscopy (FD-DOS) device, in accordance with some embodiments.

Frequency domain diffuse optical spectroscopy (FD-DOS) is a non-invasive optical imaging technique for characterizing biological tissue. FD-DOS exploits a region of the electromagnetic spectrum with relatively low absorption ranging from about 650 nanometers to 1,350 nanometers and achieves depth sensitivities up to several centimeters. The strongest molecular absorbers in this wavelength range, known as chromophores, are oxyhemoglobin, deoxyhemoglobin, water, and lipid. One advantage of FD-DOS compared to continuous-wave near infrared spectroscopy is the ability to directly measure tissue optical scattering, and thus provide a quantitative measurement of chromophore concentrations that can be compared longitudinally and between individuals. This functional information extracted from deep (up to three centimeter) tissue volumes has shown promise in areas including monitoring chemotherapy treatments of breast cancer, optical mammography, and brain imaging. For example, in breast oncology, FD-DOS is able to distinguish benign and malignant lesions by measuring concentrations of deoxy/Oxy-hemoglobin (Hb, HHb), water, and lipid levels. FD-DOS is also effective in quantifying breast density, which is critical considering women with dense breast tissue are four to six times more likely to develop breast cancer. An additional application of FD-DOS in breast oncology is monitoring response to neoadjuvant chemotherapy.

FD-DOS samples tissue volumes with radio frequency (RF)-modulated light (about 50 megahertz to 500 megahertz). Highly attenuated light, due to optical absorption and scattering, is detected at a fixed distance from the source in a reflection or transmission geometry with an optical detector. The overall sensitivity of an FD-DOS system is typically limited by the sensitivity and dynamic range of its optical detector. If the sensitivity and dynamic range of the optical detector in an FD-DOS system is increased, it enables detection of wider optical property ranges and increased source-detector (S/D) separations for higher depth sensitivity.

Some current FD-DOS designs use avalanche photodiodes (APDs) as optical detectors because of their small size and built-in amplification. APDs have an intrinsic gain of about 100× and low dark currents, leading to excellent signal-to-noise ratios (SNRs). APDs, however, require about 200 volts to 500 volts of reverse bias in order to achieve this gain. Other current FD-DOS designs use photomultiplier tubes (PMTs) as optical detectors because they have extremely high intrinsic gains of about $10^4\times$ to $10^9\times$ and low dark currents. PMTs, however, require a larger footprint size, are sensitive to magnetic fields, and require a high bias voltage (about 1 kilovolt). In both cases (APDs and PMTs), supplying a high-voltage bias requires high-voltage converters with large footprints (greater than 7 cubic centimeters), limiting their suitability for portable FD-DOS systems.

Some embodiments of the systems and methods described herein utilize silicon photomultipliers (SiPMs) (also known as multipixel photon counters, MPPCs) as an optical detector for FD-DOS. SiPMs are composed of many small microcells operating in single-photon counting mode known as single-photon avalanche diodes (SPADs), which are organized into larger arrays of about 500 to 58,000 microcells. The array is biased above breakdown voltage so that the optical detector operates in Geiger mode. SiPMs have similar high intrinsic gain (about $10^5\times$ to $10^7\times$), dark current, and signal-to-noise ratio as PMTs while operating at a much lower reverse bias (about 20 volts to 50 volts). This allows for high-voltage modules with extremely small footprints (about 0.1 cubic centimeters), which is advantageous for designing compact and portable FD-DOS systems. Further, SiPMs have about 10 to 30 decibels greater signal to noise ratios than comparably sized APDs while detecting about 1.5 to 2 orders of magnitude lower light levels, down to about 4 picowatts at 50 megahertz modulation. The greater signal to noise ratios of SiPMs as compared to APDs enables extended source-detector (S/D) separations and increased depth penetration. For example, SiPMs can accurately recover optical properties in a reflectance geometry at S/D separations up to 48 millimeters in phantoms mimicking human breast tissue. SiPMs can operate with optical wavelengths up to about 1,100 nanometers.

FIG. 1 illustrates an example embodiment of an FD-DOS device 100 with an SiPM. In FIG. 1, the FD-DOS device 100 directs modulated light at tissue 105, and processes a detected optical signal that results from absorption and scattering of the modulated light by the tissue 105. The FD-DOS device 100 illustrated in FIG. 1 includes a radio frequency signal generator 110, a driver 115, a light source 120, a silicon photomultiplier 125, an analog to digital conversion circuit 130, an electronic processing circuit 135, a battery module 140, orientation sensors 145, and a communication module 150. In some embodiments, the FD-DOS device 100 includes more or less components than the ones illustrated in FIG. 1. For example, in some embodiments, the FD-DOS device 100 may not include the battery module 140, the orientation sensors 145, and/or the communication module 150.

The radio frequency signal generator 110 is coupled to the driver 115, which drives the light source 120 for exposing the tissue 105 to modulated light at a plurality of different wavelengths and a plurality of different modulation frequencies. The silicon photomultiplier 125 detects optical signals emanating (for example, reflecting) from within the tissue 105 in response to the modulated light. The silicon photomultiplier 125 generates analog detection signals indicative of amplitude and phase of radio frequency modulation components of the detected optical signals. The analog to digital conversion circuit 130 is coupled to the silicon photomultiplier 125 and generates digital sample values from the analog detection signals.

Figure 2:
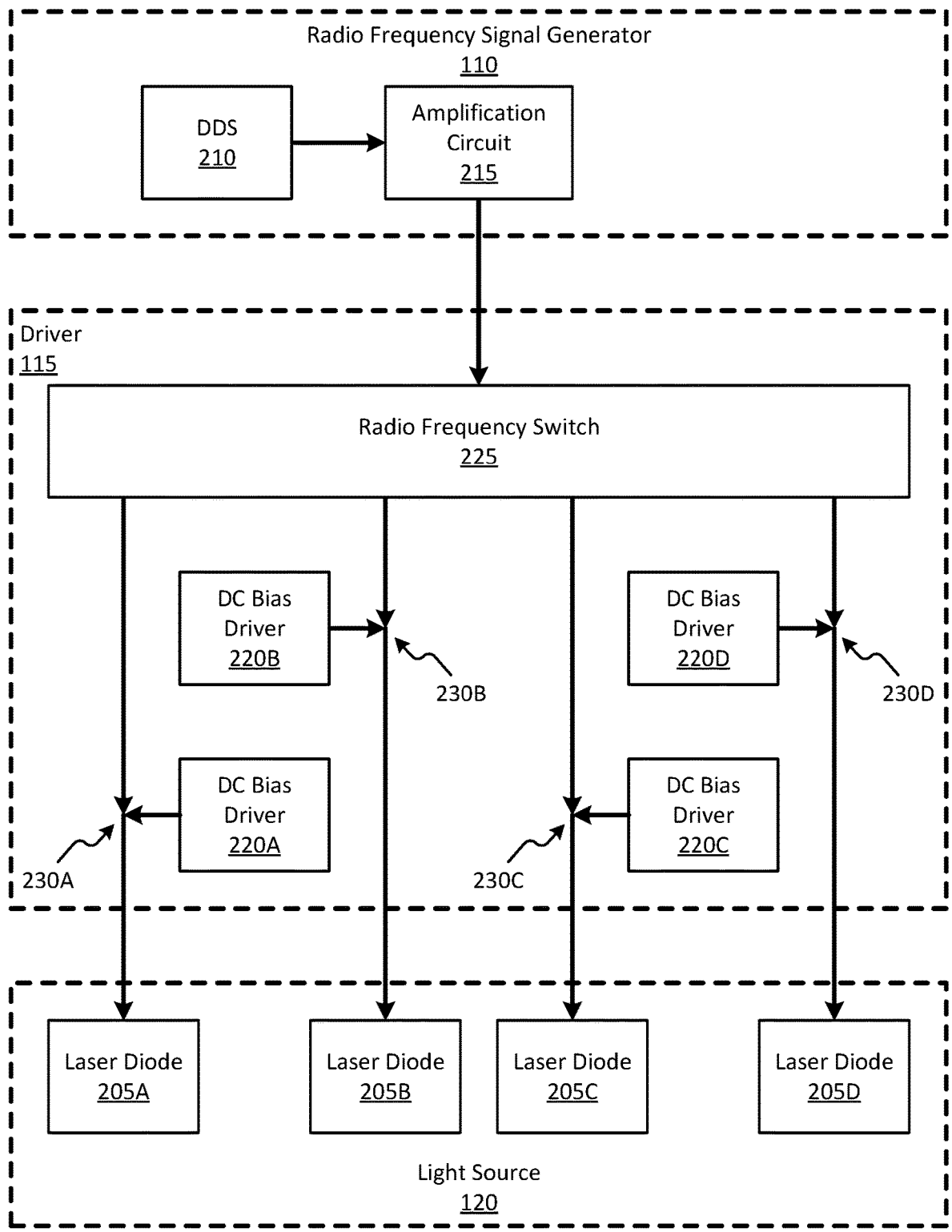
FIG. 2 is a diagram of a radio frequency signal generator, a driver, and a light source included in the FD-DOS device of FIG. 1, in accordance with some embodiments.

In some embodiments, the light source 120 includes a plurality of lasers to generate modulated light to illuminate the tissue 105. A radio frequency source and a direct current (DC) source are used together to drive the plurality of lasers to generate modulated light. FIG. 2 illustrates an example embodiment in which the light source 120 includes four laser diodes 205A through 205D. Each of the four laser diodes 205A through 205D is configured to emit a distinct wavelength of light. For example, in some embodiments, the wavelengths of the four laser diodes 205A through 205D are 681 nanometers, 783 nanometers, 823 nanometers, and 850 nanometers, respectively.

The radio frequency signal generator 110 illustrated in FIG. 2 acts as a radio frequency source and includes a direct digital synthesizer (DDS) 210 and an amplification circuit 215. The DDS 210 is a current controlled device that outputs radio frequency modulation signals. In some embodiments, the DDS 210 communicates with the electronic processing circuit 135 (for example, via a serial peripheral interface link or another appropriate communication link) to select the output current and frequency. An example of the DDS 210 is the AD9912 DDS by Analog Devices, which generates an output current ranging from zero and 31.7 milliamps and a frequency ranging from zero and 450 megahertz. The maximum output power of the AD9912 DDS into a 50 ohm load is 7 decibal-milliwatts at 50 megahertz. The power output also may decrease with increasing output frequency. In some implementations, the plurality of laser diodes 205A through 205D need about 10 to 20 decibal-milliwatts of output power. Thus, in some embodiments, the amplification circuit 215 amplifies the output signal from the DDS 210. Alternatively, or in addition, the radio frequency signal generator 110 is configured to increase the power of the radio frequency modulation signals as a function of frequency. For example, the amplification circuit 215 may increase power of the radio frequency modulation signals generated by the DDS 210 as the frequency increases, for example, to account for additional signal loss at higher frequencies.

The driver 115 includes a plurality of DC bias drivers that act as DC sources for the laser. In FIG. 2, the driver 115 includes four DC bias drivers 220A through 220D. Each of the four DC bias drivers 220A through 220D is configured to provide a DC signal for a corresponding one of the four laser diodes 205A through 205D. An example of the DC bias driver is the MLD230CHB laser driver by Thorlabs, which delivers up to 200 milliamps with a 3 volt compliance voltage. The MLD230CHB laser driver exhibits excellent stability with 12 microamp average root mean square current resulting in microwatt laser power stability.

The driver 115 also includes a radio frequency switch 225 to route the radio frequency modulation signal from the radio frequency signal generator 110 to each of the four laser diodes 205A through 205D. In some embodiments, the radio frequency switch 225 includes a plurality of cascade connected single pole, double throw switches that each route signals from one input to two output paths. Alternatively, the radio frequency switch 225 includes one or more multiport switches (or single pole, multiple throw switches) that each route signals from one input to three or more output paths. The driver 115 illustrated in FIG. 2 also includes four bias tees 230A through 230D to isolate the radio frequency modulation signals from the radio frequency signal generator 110 and the DC signals from the four DC bias drivers 220A through 220D.

Returning to FIG. 1, the silicon photomultiplier 125 (also known as a multi-pixel photon counter) detects optical signals emanating from the tissue 105 in response to the modulated light generated by the light source 120. The silicon photomultiplier 125 generates analog detection signals indicative of amplitude and phase of radio frequency modulation components of the detected optical signals. Unlike APDs which require additional amplification and high bias voltages, the silicon photomultiplier 125 does not require additional amplification and a much lower bias voltage which translates into a significant size reduction. As the bias voltage for the silicon photomultiplier 125 is low, an ultra-compact high voltage module can be used. An example high-voltage module is the C14156 high-voltage module by Hamamatsu Photonics, which has a footprint of 7×7×2 millimeters and is capable of providing up to 80 volts (2 milliamps) with only 1 millivolt peak-to-peak ripple.

The analog to digital conversion circuit 130 is coupled to the silicon photomultiplier 125 and includes an analog to digital converter (ADC) for sampling the analog detection signals generated by the silicon photomultiplier 125. The analog to digital converter generates digital sample values from the analog detection signals (for example, via resistive termination). The analog to digital converter is also AC coupled to the radio frequency signal generator 110 to receive and sample the RF modulation signals generated by the radio frequency signal generator 110. The analog to digital converter generates digital reference values from the radio frequency modulation signals. An example of the analog to digital converter is the AD9613 by Analog Devices, which is a 12 bit 250 MHz dual channel low voltage differential signal (LVDS) device with a 1.8 volt peak to peak input capability. The AD9613 has a dynamic range of about 70 decibels. In some embodiments, the analog to digital conversion circuit 130 is configured to under-sample the analog detection signals. Although the ADC sampling rate can be well below the Nyquist sampling frequency for the maximum system frequency (i.e., about 400 megahertz), the small bandwidth of the input signal allows the analog to digital conversion circuit 130 to meet the Nyquist-Shannon sampling criterion.

The electronic processing circuit 135 illustrated in FIG. 1 includes a field programmable gate array (FPGA) 155 and memory 160. The memory 160 is coupled to the FPGA 155. The memory 160 includes read only memory (ROM), random access memory (RAM), an electrically erasable programmable read-only memory (EEPROM), other non-transitory computer-readable media, or any combination thereof. The FPGA 155 is configured to retrieve program instructions and data from the memory 160 and execute, among other things, instructions to perform the methods described herein. Alternatively of in addition, the memory 160 is included in the FPGA 155. The FPGA 155 includes routines for transferring information between components within the electronic processing circuit 135 and other components of the FD-DOS device 100. In some embodiments, in addition to (or in place of) the FPGA 155, the electronic processing circuit 135 includes an electronic processor (for example, a microprocessor).

The electronic processing circuit 135 is coupled to the analog to digital conversion circuit 130 and receives digital sample values and digital references values from the analog to digital conversion circuit 130. The electronic processing circuit 135 is configured to determine absorption values and scattering values based on the digital sample values. In some embodiments, in order to readily obtain amplitude and phase responses at each of the RF modulation frequencies, the FD-DOS device 100 obtains a large number of digital sample values for each set of RF modulation frequencies, and the electronic processing circuit 135 processes each set of digital sample values into a frequency domain representation using a Fourier transform. In some embodiments, the electronic processing circuit 135 uses a full fast Fourier transform (FFT) to determine the amplitude and phase responses from the digital sample values. Alternatively or in addition, the electronic processing circuit 135 uses a Goertzel algorithm to determine the amplitude and phase responses from the digital sample values faster than with a full FFT.

Figure 3A:
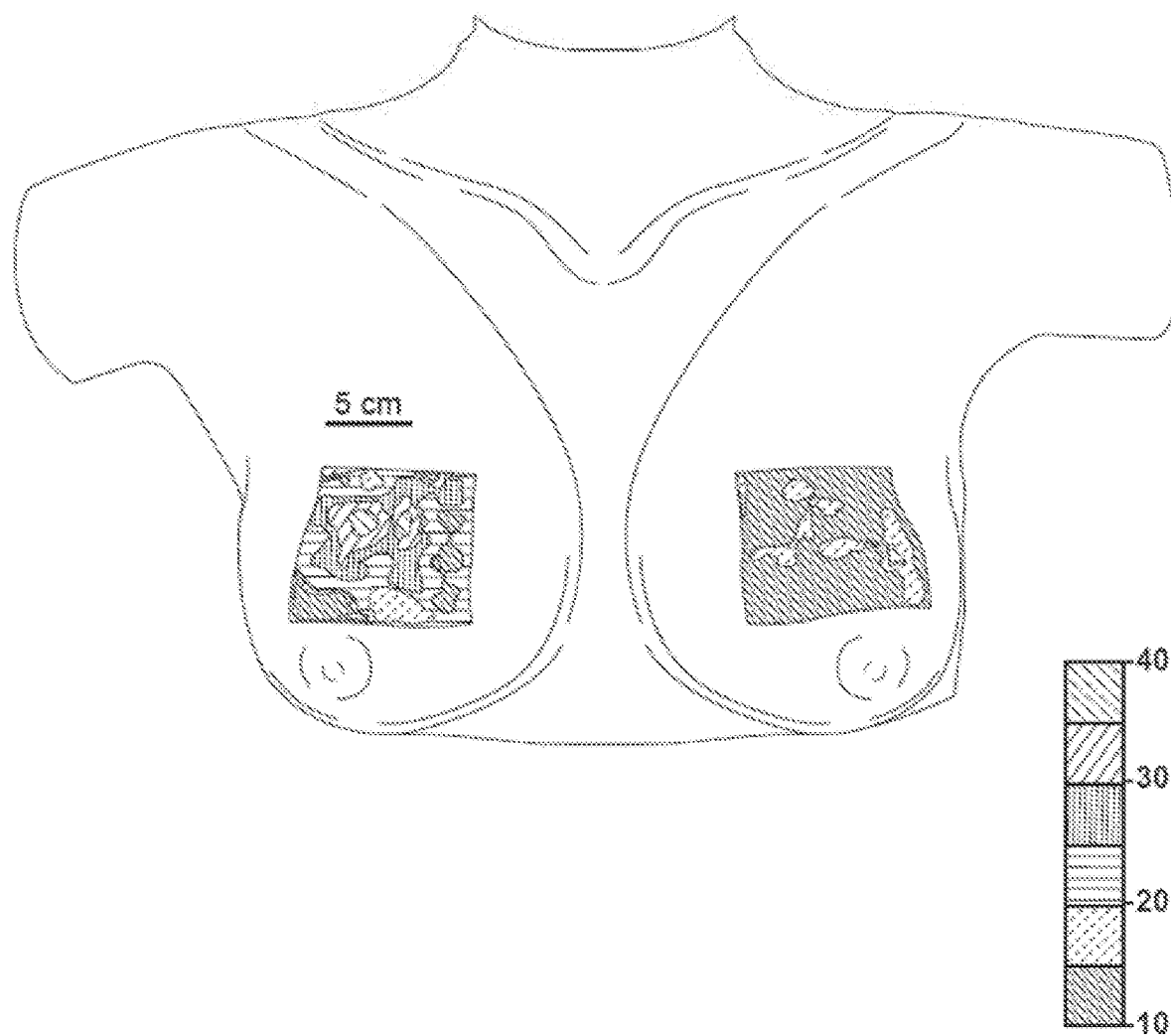
FIG. 3A are examples of oxy-hemoglobin (ctHb) images of breast tissue.

The electronic processing circuit 135 is also configured to determine concentration values (for example, chromophore concentrations) based on the absorption values and the scattering values. For example, the electronic processing circuit 135 determines chromophore concentration by using the Beer-Lambert law in combination with absorption values and predetermined molar extinction coefficients. The electronic processing circuit 135 is also configured to determine an image stream based on the concentration values. For example, the electronic processing circuit 135 uses the concentration values to build bi-cubic interpolated images. FIG. 3A are examples of oxy-hemoglobin (ctHb) images for breast tissue. The ctHb image on the left side of FIG. 3A is of cancerous tissue with an identifiable tumor. The ctHb image on the right side of FIG. 3A is of a healthy contralateral breast. In some embodiments, the electronic processing circuit 135 is configured to generate an image stream with a frame rate that is greater than thirty hertz (i.e., a real-time image stream). In some embodiments, the electronic processing circuit 135 is configured to capture data, process the data, and display the data in real-time.

Figure 3B:
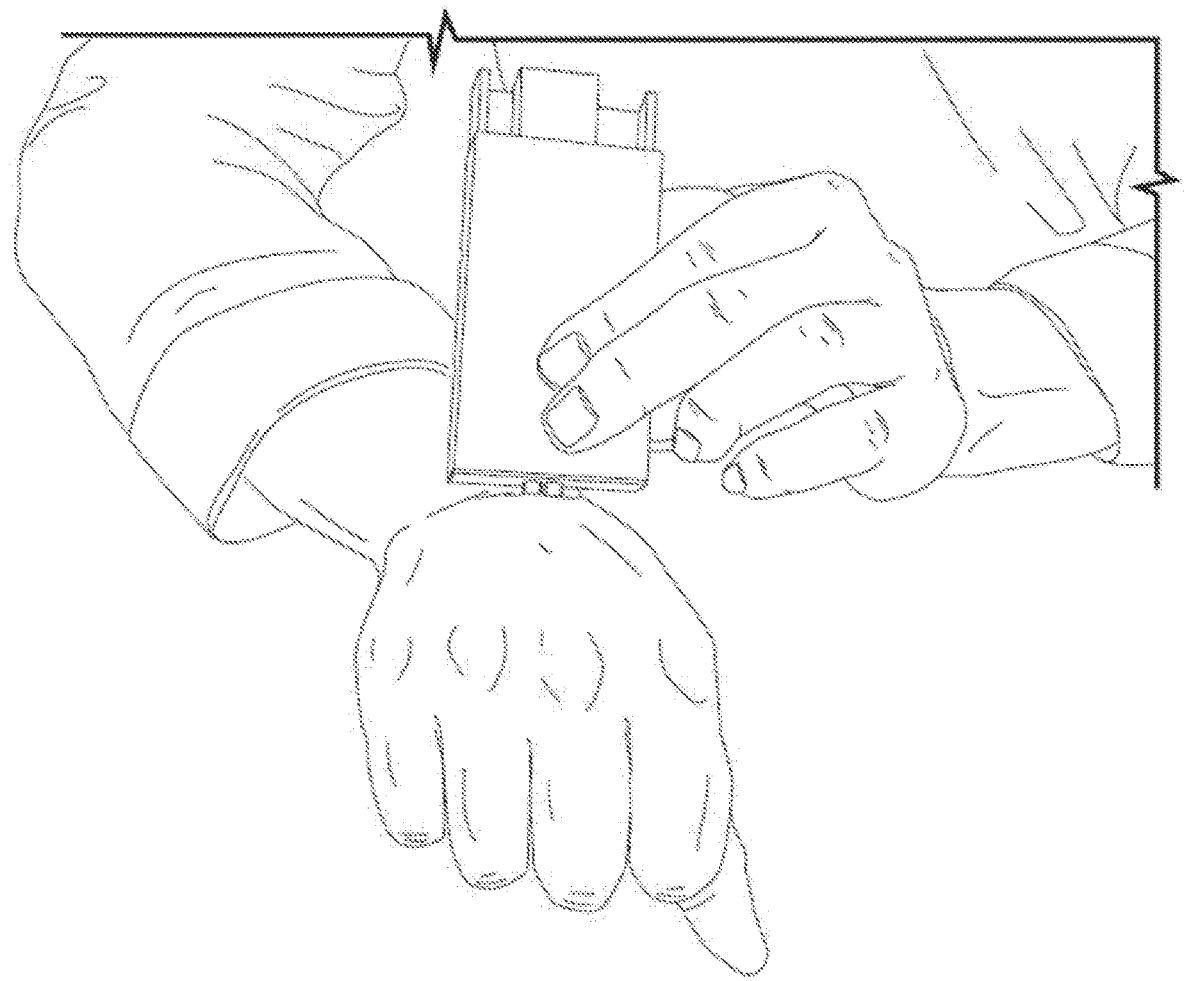
FIG. 3B is an example of a handheld housing for an FD-DOS device, in accordance with some embodiments.

In the embodiment illustrated in FIG. 1, the FD-DOS device 100 is powered by the battery module 140. The battery module 140 includes one or more batteries or battery packs. In some such embodiments, the components of the FD-DOS device 100 (for example, the radio frequency signal generator 110, the driver 115, the light source 120, the silicon photomultiplier 125, the analog to digital conversion circuit 130, the electronic processing circuit 135, and the battery module 140) are mounted in a housing that is sized to be handheld. FIG. 3B is an example embodiment of a handheld housing for the FD-DOS device 100. The dimensions of the handheld housing illustrated in FIG. 3A are 3 inches by 4.5 inches by 1 inch. Alternatively, or in addition, the FD-DOS device 100 is powered by mains power having nominal line voltages between, for example, 100 volts and 240 volts AC and frequencies of approximately 50 hertz to 60 hertz.

The orientation sensors 145 are configured to generate orientation signals indicative of the orientation and/or position of the FD-DOS device 100. The orientation sensors 145 include gyroscopes, accelerometers, magnetometers, optical tracking sensors, or a combination thereof. In some embodiments, the electronic processing circuit 135 is also configured to correlate the orientation signals to the image stream.

The communication module 150 sends and/or receives signals to and/or from one or more separate communication modules. Signals include, for example, information, data, serial data, data packets, concentration values, image streams, and orientation signals. The communication module 150 is coupled to one or more separate communication modules via wires, fiber, and/or wirelessly. Communication via wires and/or fiber can be any appropriate network topology known to those skilled in the art (for example, Ethernet). Wireless communication can be any appropriate wireless network topology known to those skilled in the art (for example, Wi-Fi and Bluetooth™).

Figure 3C:
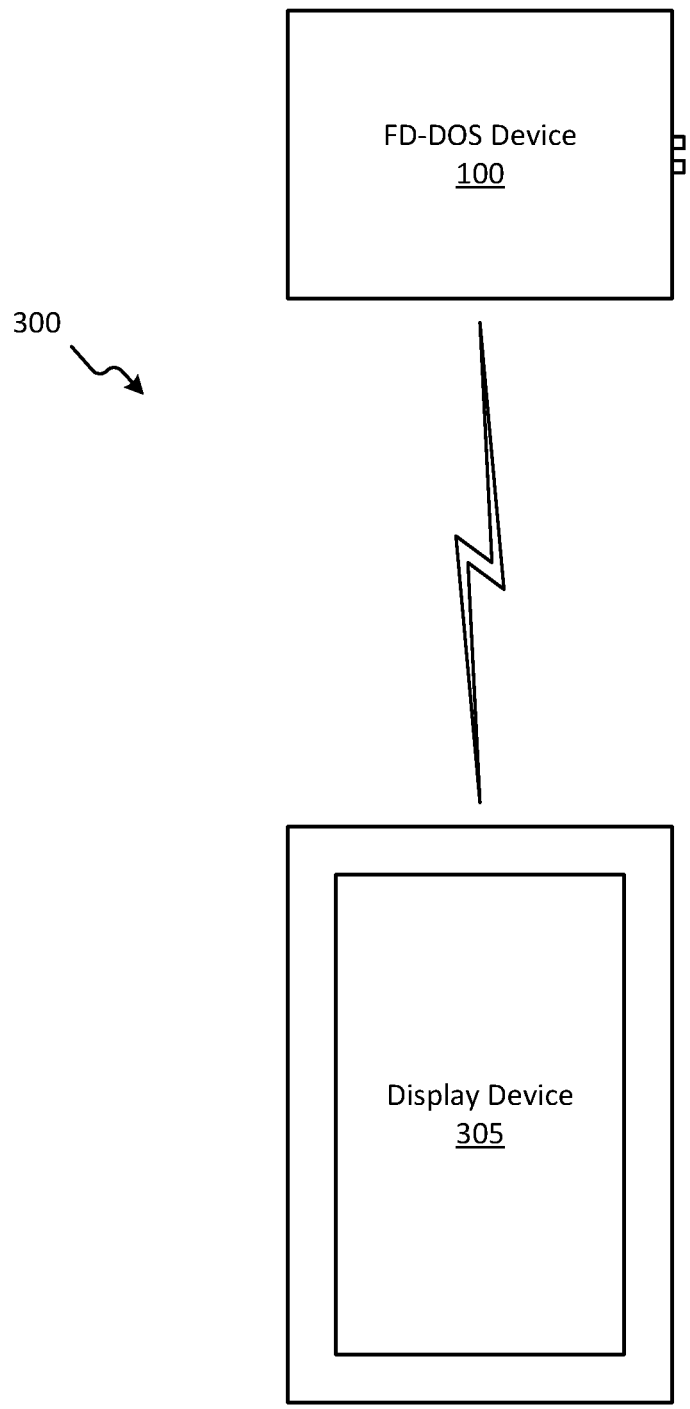
FIG. 3C is a diagram of an FD-DOS system, in accordance with some embodiments.

FIG. 3C illustrates an example embodiment of an FD-DOS system 300. The FD-DOS system 300 illustrated in FIG. 3C includes the FD-DOS device 100 and a display device 305. The display device 305 is configured to receive and display the image stream. The display device 305 includes, for example, a mobile phone, a tablet, a laptop, a desktop, or a server. The display device 305 communicates with the FD-DOS device 100 via wires, fiber, and/or wirelessly.

Table 1 illustrates a comparison of physical and electrical characteristics between the SensL MicroRB-10020 by ON Semiconductor (an example of a "SiPM") and the S12060-10 by Hamamatsu (an example of an "APD").

TABLE 1

COMPARISON OF SIPM AND APD

| Optical Detector | Photo-sensitive Area | Operating Voltage | PDE at 650 nm | PDE at 850 nm | Gain | Dark Current | Excess Noise Factor |
|---|---|---|---|---|---|---|---|
| SiPM | 0.63 mm$^2$ | 33 volts | 27% | 12.5% | 1.5e6 | 831 nA | 1.19 |
| APD | 0.785 mm$^2$ | 250 volts | 85% | 60% | 100 | 10 nA | 3.98 |

Figure 4A:
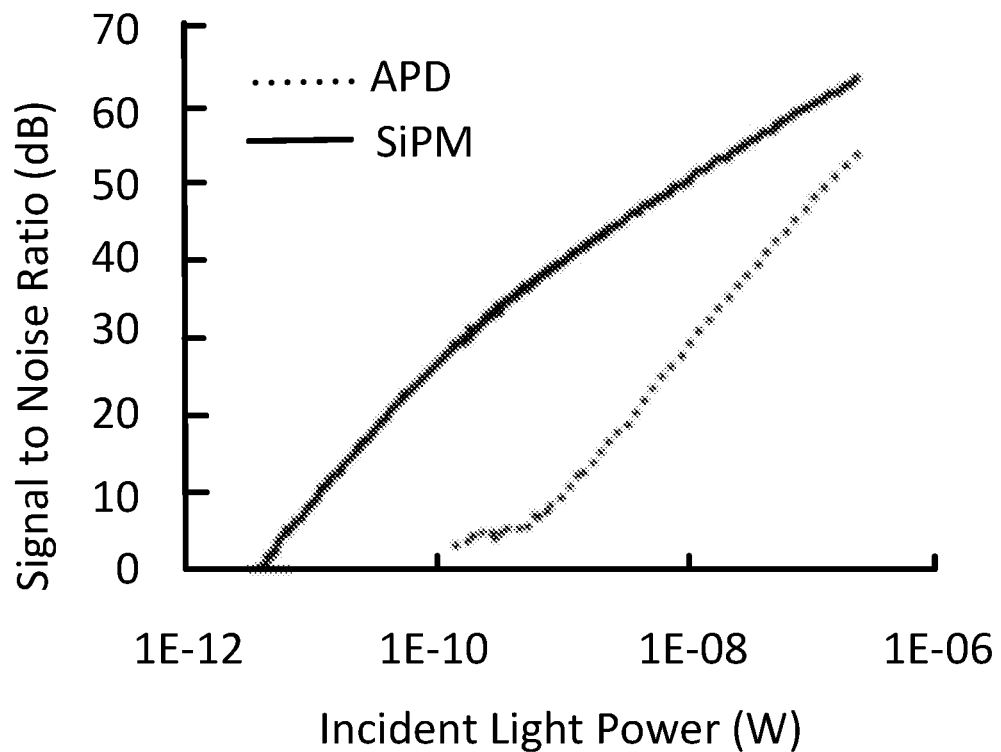
FIG. 4A is a graph that represents example signal to noise ratios of an avalanche photo diode and a silicon photomultiplier.

FIG. 4A is a graph of example signal to noise ratios (SNRs) of an APD and a SiPM as a function of input at a radio frequency modulation frequency of 50 megahertz. The signal to noise ratios illustrated in FIG. 4A were obtained by biasing a 660 nanometer edge-emitting laser diode with a direct current (DC) from a laser driver and radio frequency power from a vector network analyzer (VNA). The modulated light was collimated, passed through a variable optical density filter wheel, and fiber-coupled to the optical detector. The graph in FIG. 4A characterizes the signal to noise ratios of the S12060-10 and the SensL MicroRB-10020 listed above in Table 1 at a 50 megahertz radio frequency modulation frequency. No pre-amplification module was used and each type of optical detector was connected directly to a 50 ohm input of the VNA. As illustrated in FIG. 4A, the signal to noise ratio of the SiPM is about 10 decibels to 30 decibels greater than the signal to noise ratio of the APD at 50 megahertz and depends upon the incident optical power. As also illustrated in FIG. 4A, the SiPM's signal to noise ratio advantage increases with lower input powers and reaches zero at about 1.5 to 2 orders of magnitude lower input power than the APD. Further, the SiPM's photo response is non-linear.

Figure 4B:
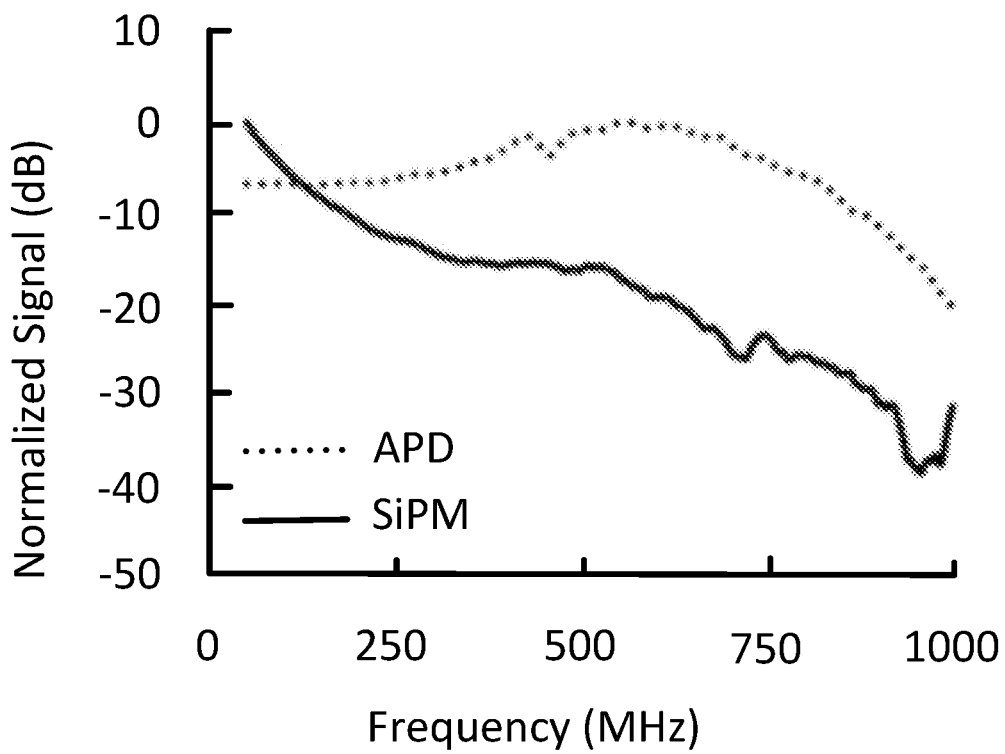
FIG. 4B is a graph that represents example normalized frequency responses of an avalanche photo diode and a silicon photomultiplier.

The bandwidths of each type of optical detector was measured by recording optical detector radio frequency output amplitude as a function of frequency with the VNA. FIG. 4B shows an example of each type of optical detector's normalized (to the maximum signal) frequency response. Normalization is helpful because the same absolute optical power cannot be used simultaneously for both types of optical detectors across the entire frequency range. At low attenuations, the current limit of the SiPM's power supply is reached (about 2 milliamps), while the APD is not sensitive at the higher attenuations. From FIG. 4B, it is observed that the APD has a better normalized frequency response than the SiPM. For example, the normalized frequency response of the SiPM in FIG. 4B decays at about 10 decibels at 500 megahertz.

In FD-DOS, diffuse RF-modulated light reaching the optical detector after propagation through tissue lags in phase and is diminished in amplitude. This phase lag and amplitude reduction is related to the optical properties of the sample via the radiative transport equation (RTE). A P1 semi-infinite approximation to the RTE can be used to fit the measured phase and amplitude and estimate the sample's optical properties. The fitting can be done, for example, using a Levenberg-Marquardt least squares minimization algorithm.

To more accurately fit the measured data, the amplitude reduction and phase lag should be attributed to the sample, and not the instrumentation (for example, frequency response/attenuation of the RF cables and electronic components). Current calibration methods require that the optical detector has a linear response with optical power. Current FD-DOS systems compensate for the linear response requirements of current calibration methods by limiting the range of frequencies scanned during a frequency sweep. For example, current FD-DOS system that use APDs limit the range of the optical powers scanned during a frequency sweep to optical powers in which the APDs have a linear response. Limiting the range of optical powers scanned during a frequency sweep limits the dynamic range of the optical detector. Further, since the amplitude response of a SiPM is non-linear, a more intricate calibration is needed.

Figure 5:
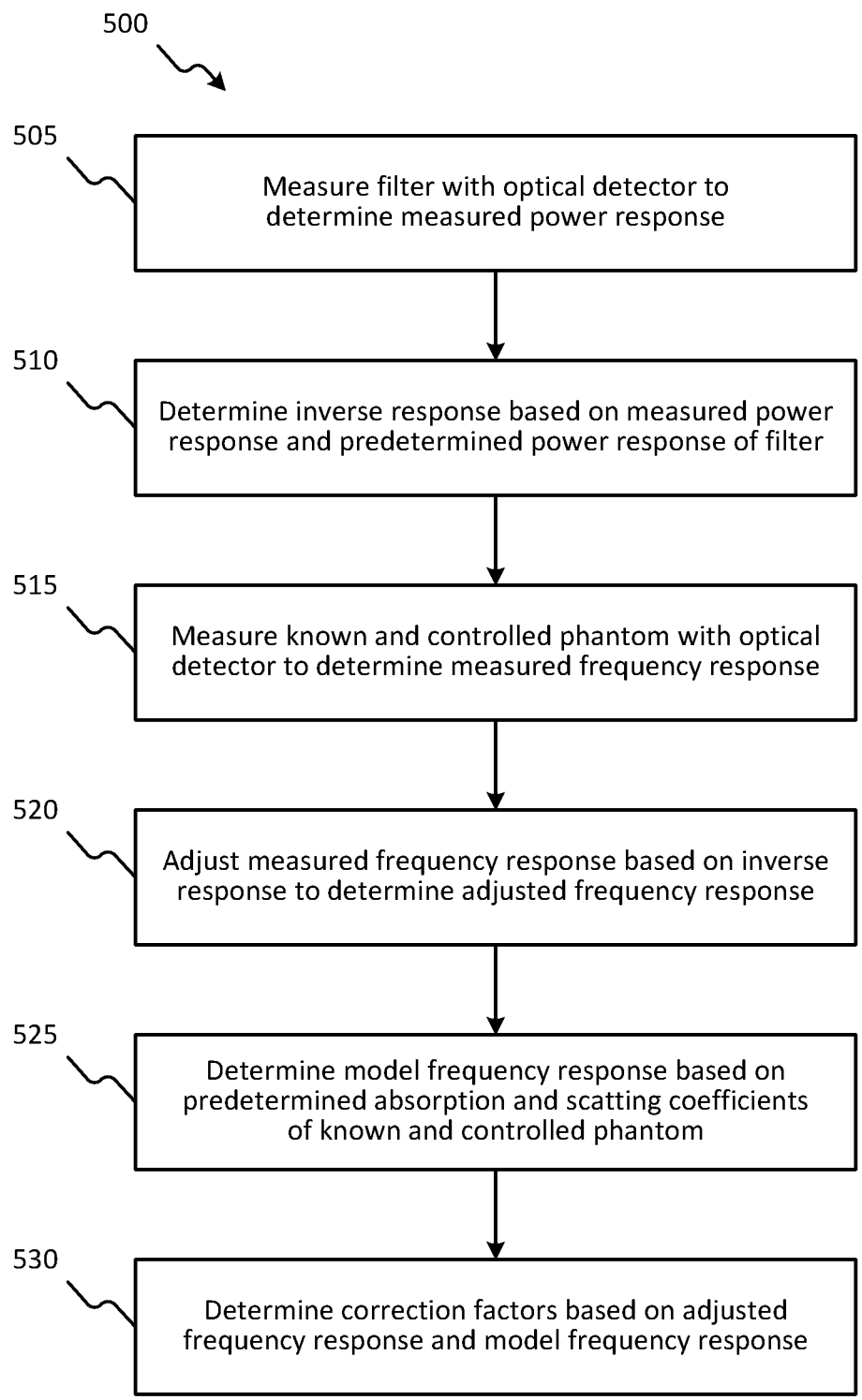
FIG. 5 is a flowchart of a method for calibrating an optical detector, in accordance with some embodiments.
Figure 6A:
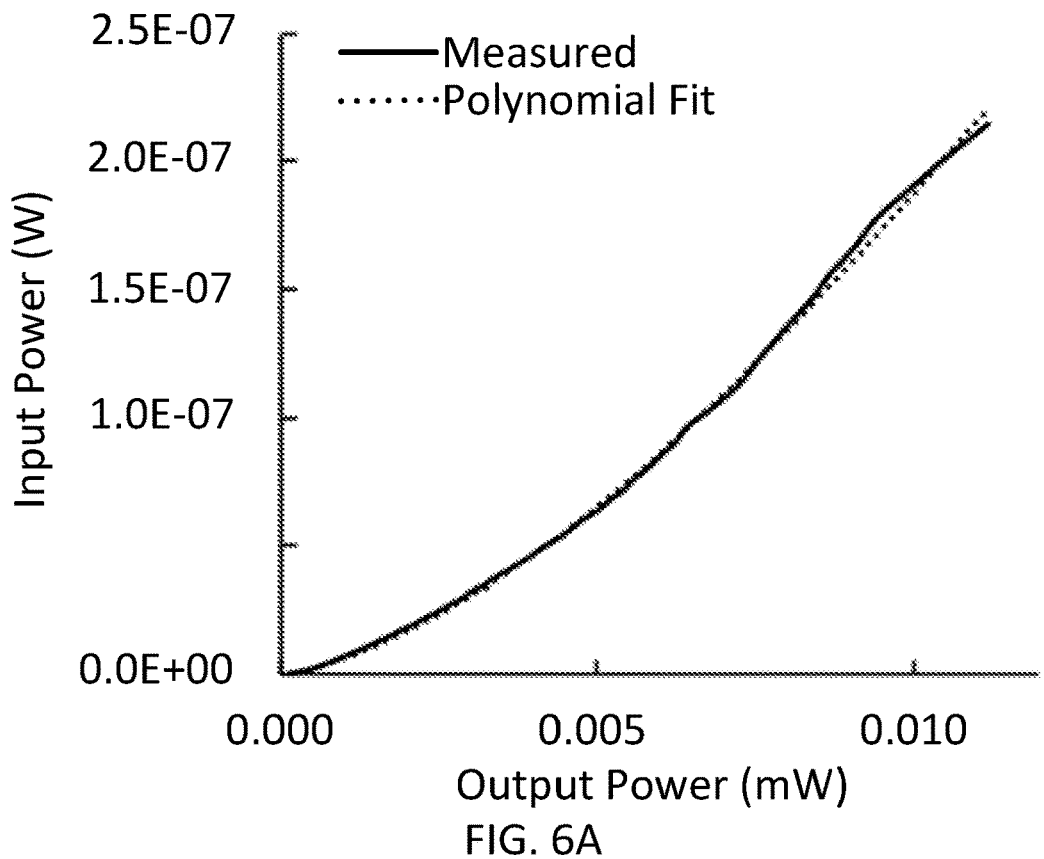
FIG. 6A is a graph that represents an example of a measured power response of a continuously variable intensity filter.
Figure 6B:
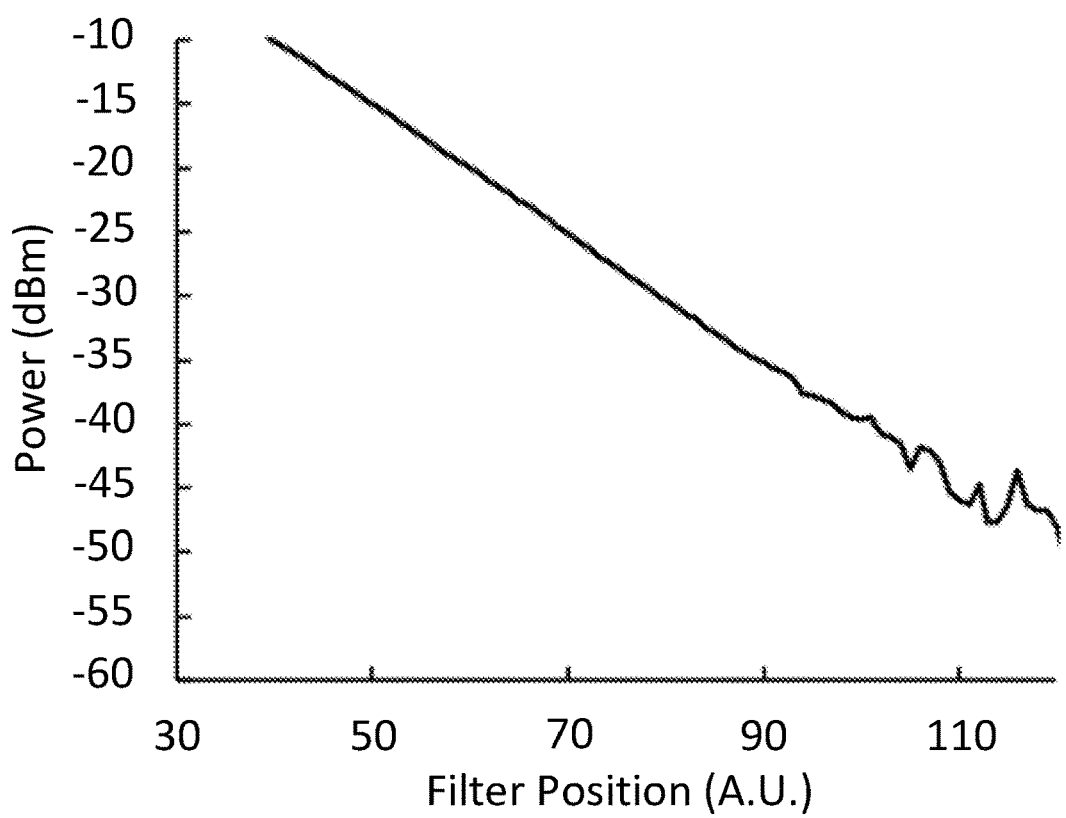
FIG. 6B is a graph that represents an example of a predetermined power response of a continuously variable intensity filter.
Figure 6C:
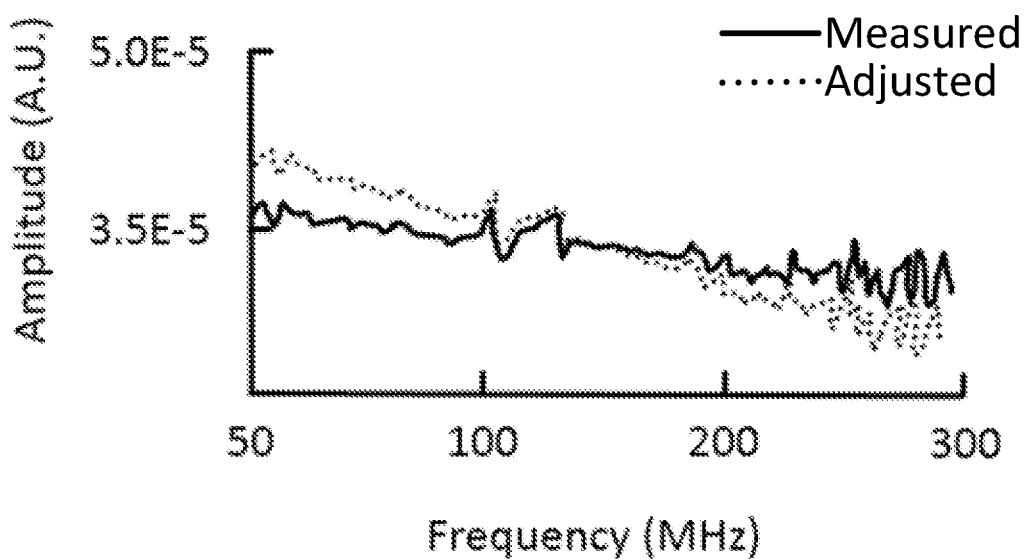
FIG. 6C is a graph that represents examples of a measured and an adjusted frequency response of a known and controlled phantom.
Figure 6D:
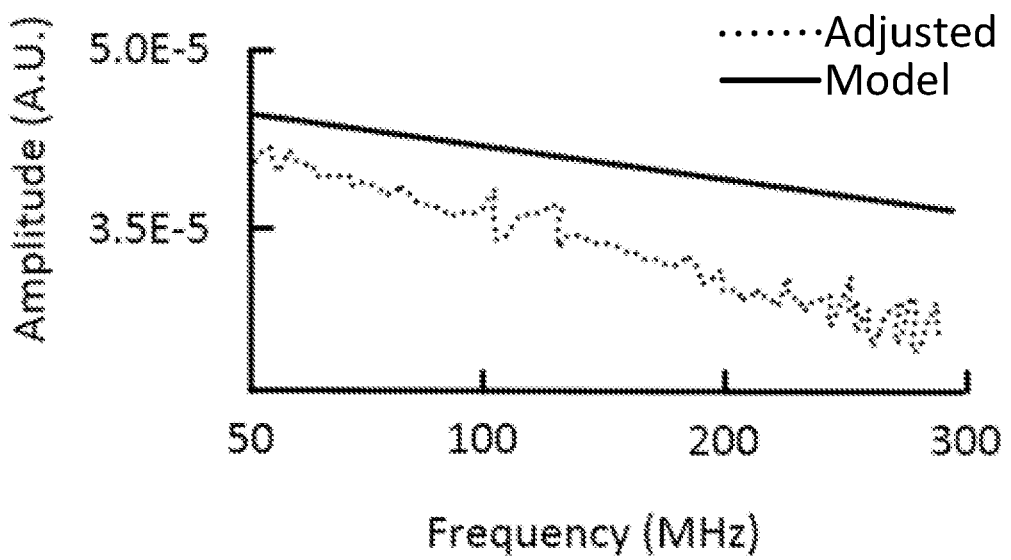
FIG. 6D is a graph that represents examples of an adjusted and a model frequency response of a known and controlled phantom, in accordance with some embodiments.

FIG. 5 is an example of a method 500 for calibrating an optical detector (such as a SiPM) in a DOS device (such as FD-DOS 100). The method 500 enables any non-linear optical detector to be used in FD-DOS, so long as the response does not change. At block 505, a filter (for example, a continuously variable intensity filter) (an example of a "first sample") is measured with the optical detector to determine a measured power response. For example, the optical response of a variably attenuating filter is measured with a calibrated optical detector to determine the measured power response. FIG. 6A is an example of a measured power response of a continuously variable intensity filter. At block 510, an inverse response is determined based on the measured power response and a predetermined power response of the filter. The inverse response represents the power response of attenuated signals through the filter. In some embodiments, the inverse response is determined by fitting the measured power response to the predetermined power response of the filter (using, for example, a polynomial fit). FIG. 6B is an example of a predetermined power response. At block 515, a known and controlled phantom (an example of a "second sample") is measured with the optical detector to determine a measured frequency response (an example of a "first frequency response"). At block 520, the measured frequency response is adjusted based on the inverse response to determine an adjusted frequency (an example of a "second frequency response"). In some embodiments, only the relative amplitude dependence on frequency is corrected to eliminate nonlinearity measured at block 510. FIG. 6C includes examples of a measured and an adjusted frequency response of a known and controlled phantom as a function of swept frequencies. At block 525, a model frequency response (an example of a "third frequency response") is determined based on predetermined absorption and scattering coefficients of the known and controller phantom. FIG. 6D includes examples of an adjusted and a model frequency response of a known and controlled phantom. The model frequency response in FIG. 6D is generated using a photon transport model based on predetermined phantom absorption and scattering coefficients. In some embodiments, the absolute amplitude and phase response is adjusted, for example, to account for power attenuations and phase delays in the system. At block 530, a plurality of correction factors are determined based on the adjusted frequency response and the model frequency response. The plurality of correction factors represent corrections for non-linear amplitude changes at different signal levels. In some embodiments, the plurality of correction factors are determined by comparing the adjusted frequency response and the model frequency response. In some embodiments, a correction factor is determined for each wavelength in a frequency sweep. For example, if a frequency sweep includes 100 frequencies, 200 correction factors are determined (i.e., 100 correction factors for amplitude and 100 correction factors for phase). In some embodiments, the frequency responses described herein with respect to the method 500 illustrated in FIG. 5 include amplitude data, phase data, or both. In some embodiments, the method 500 can be used for calibrating FD-DOS systems that include APDs or a PMTs as the optical detector.

Figure 7:
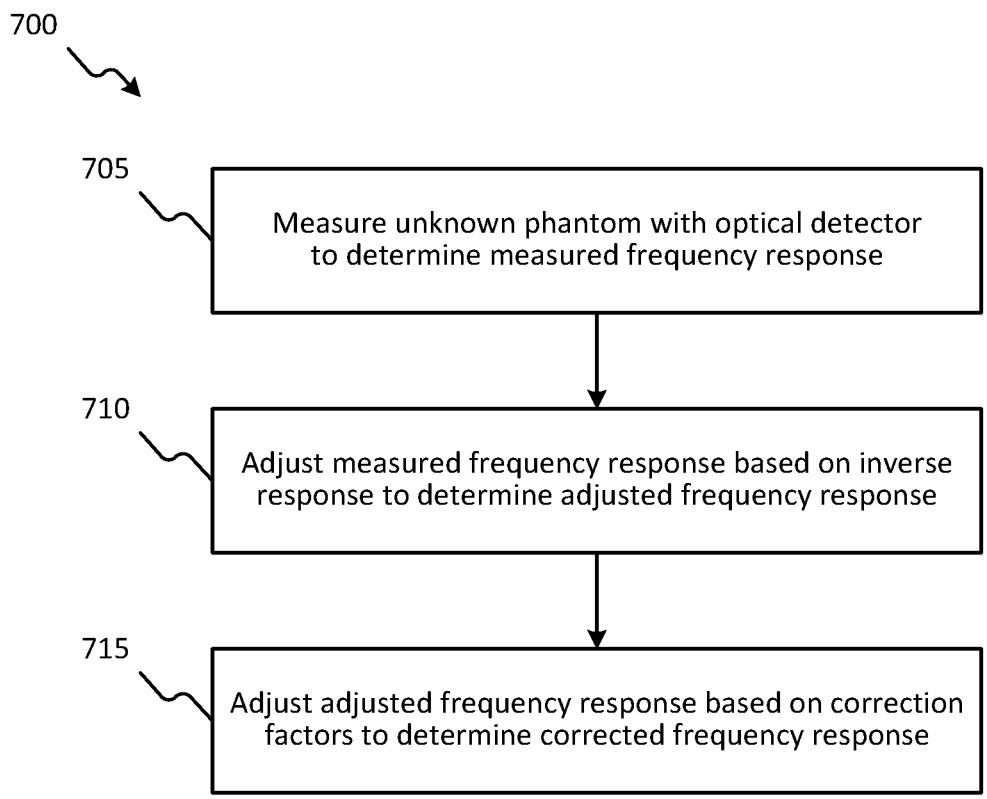
FIG. 7 is a flowchart of a method for calibrating a measured frequency response of an optical detector, in accordance with some embodiments.
Figure 8A:
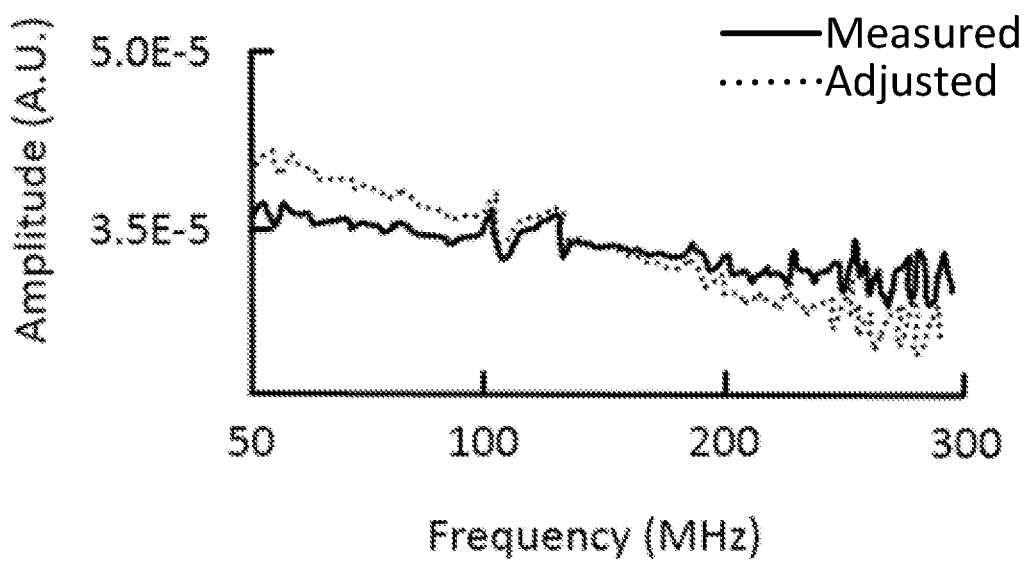
FIG. 8A is a graph that represents examples of a measured and an adjusted frequency response of an unknown phantom.
Figure 8B:
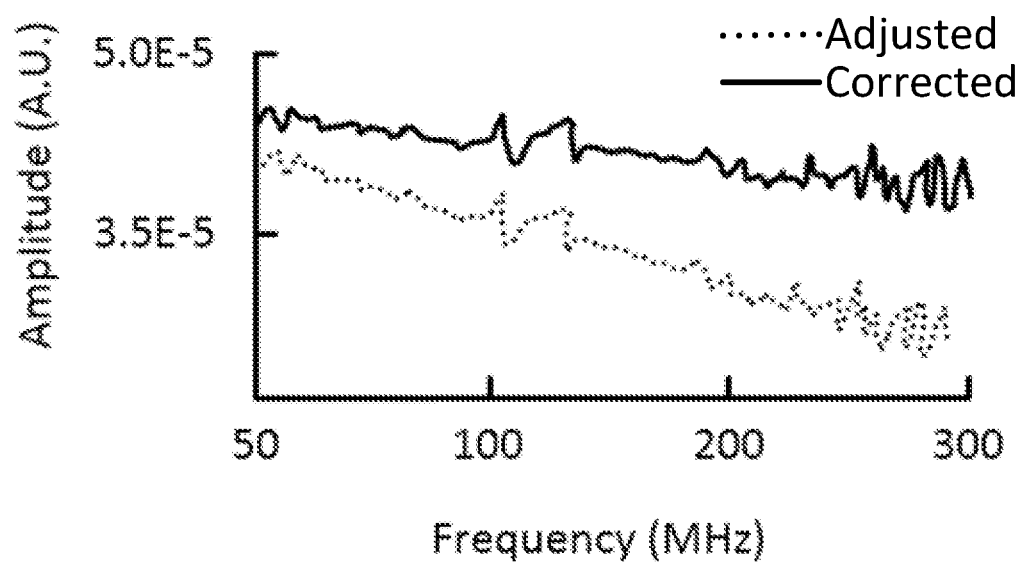
FIG. 8B is a graph that represents examples of an adjusted and a corrected frequency response of an unknown phantom, in accordance with some embodiments.

With the inverse function and the plurality of correction factors, the FD-DOS device 100 calibrates measured frequency responses to account for non-linear amplitude changes at different signals levels. FIG. 7 is an example of a method 700 for calibrating a measured frequency response of an optical detector (such as the SiPM) in a DOS device to account for non-linear amplitude changes at different signals levels. The method 700 can be an extension to method 500 to confirm the accuracy of the calibration. In addition, the method 700 can be used by the electronic processing circuit 135 for real-time calibration. At block 705, an unknown phantom (for example, a tissue sample) (an example of a "third sample") is measured with the optical detector to determine a measured frequency response (an example of a "fourth frequency response"). At block 710, the measured frequency response is adjusted based on the inverse response to determine an adjusted frequency response (an example of a "fifth frequency response"). FIG. 8A includes examples of a measured and an adjusted frequency response of an unknown phantom. At block 715, the adjusted frequency response is adjusted based on the plurality of correction factors to determine a corrected frequency response (an example of a "sixth frequency response"). FIG. 8B includes examples of an adjusted and a corrected frequency response of an unknown phantom. In some embodiments, the method 700 can be used for calibrating FD-DOS systems that include APDs or a PMTs as the optical detector.

Figure 9:
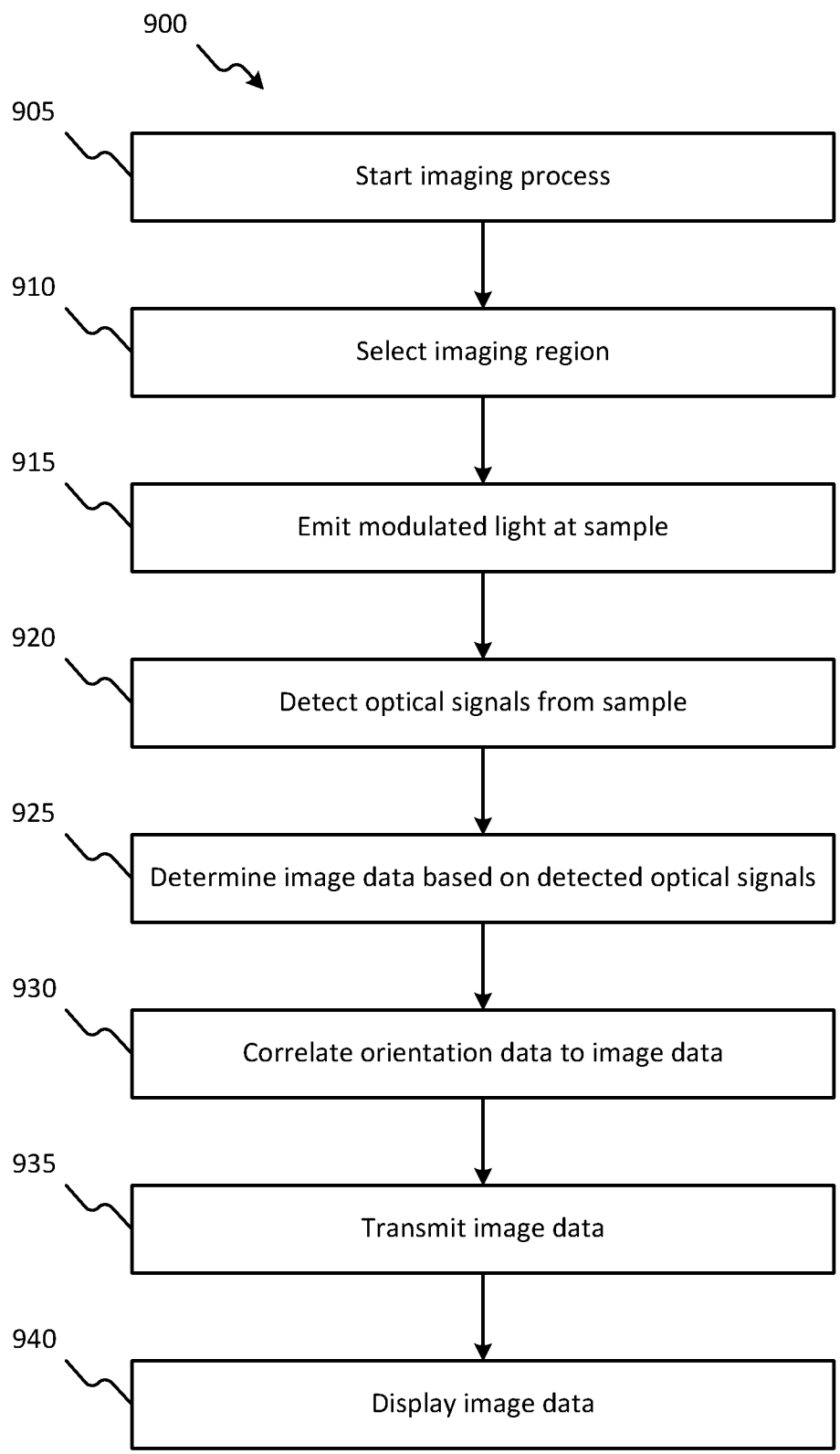
FIG. 9 is a flowchart of a process for imaging a sample with frequency domain diffuse optical spectroscopy, in accordance with some embodiments.

FIG. 9 is an example of a process 900 for imaging a sample with FD-DOS. For ease of description, the process 900 is described below in relation to the FD-DOS system 300 illustrated in FIG. 3. At block 905, the process 900 is started via user input. For example, a user initiates the process 900 by providing user input to the display device 305. At block 910, the imaging region is selected. For example, a user paints an image using the FD-DOS device 100, in any direction, displayed in real-time on the display device 305 and tracked via the orientation sensors 145. At block 915, the FD-DOS device 100 emits modulated light at the sample (for example, at tissue 105). In some embodiments, the FD-DOS device 100 performs a frequency sweep in the 10 hertz to 400 megahertz range (with a user defined step size) and modulates each of the four laser diodes 205A through 205D in sequential order. At block 920, the FD-DOS device 100 detects optical signals emanating from the sample in response to the emitted modulated light. In some embodiments, up to 65,556 samples are captured per frequency per wavelength. In some embodiments, the optical detector collects scattered light, which is captured at 250 megahertz by a dual channel analog to digital converter. In some embodiments, modulation frequencies above 125 megahertz are aliased (due to a 250 megahertz ADC capture rate), however since all modulation frequencies are known, aliased frequencies in overlapping Nyquist zones are removed. At block 925, the FD-DOS device 100 determines image data based on the detected optical signals. An example of a process for determining the image data based on the detected optical signals is described below in relation to FIG. 10. At block 930, the FD-DOS device 100 correlates orientation data from the orientation sensors 145 with the image data. At block 935, the FD-DOS device transmits the image data (for example, to the display device 305). In some embodiments, the FD-DOS device 100 transmits chromophore values and orientation data to the display device 305 at about 5 to 10 megabits per second (i.e., via Bluetooth™) or at about 50 megabits per second (i.e., via Wi-Fi). At block 940, the display device 305 displays the image data in real-time (for example, at a frame rate that is greater than 30 hertz).

Figure 10:
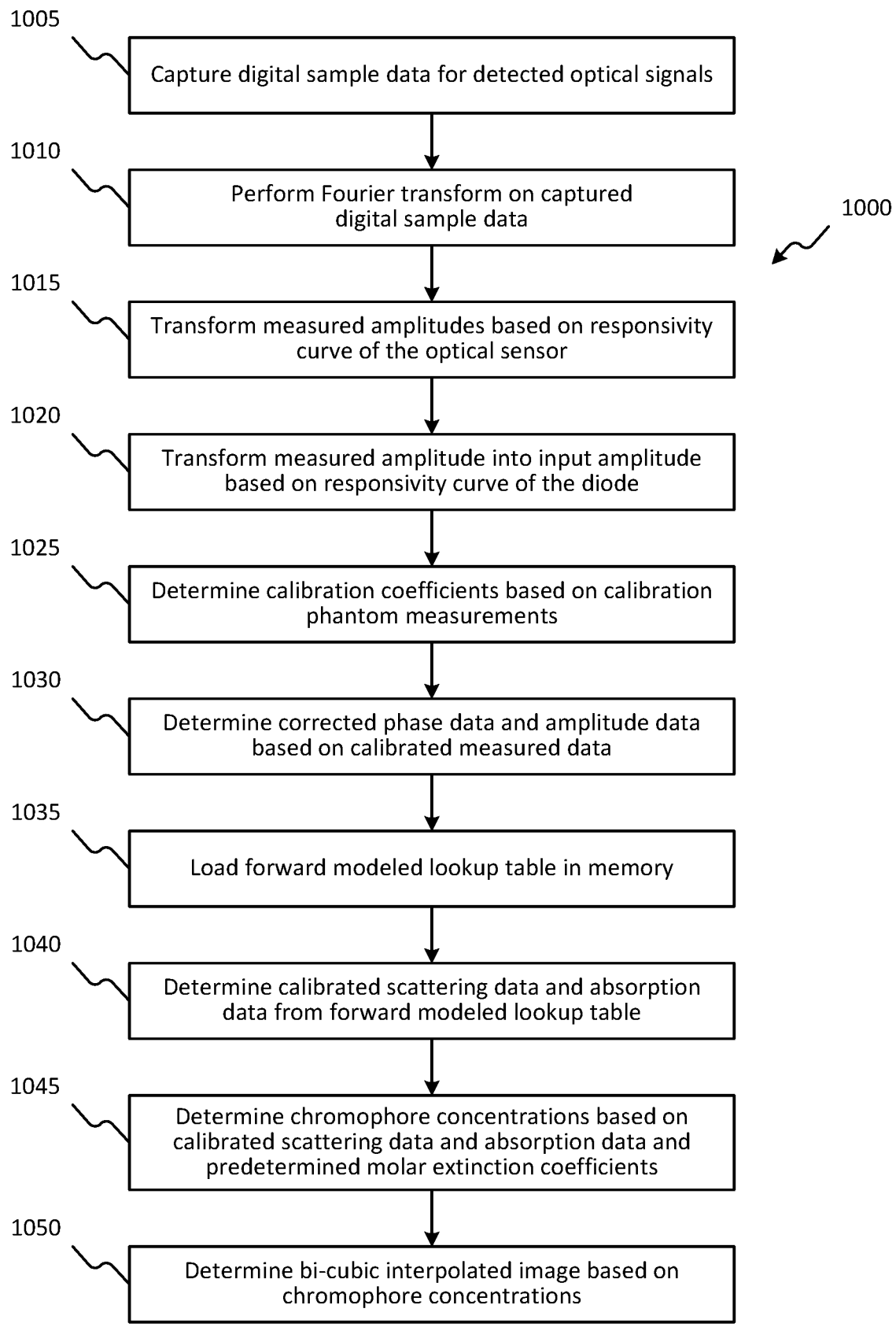
FIG. 10 is a flowchart of a process for determining image data based on optical signals detected by an optical detector, in accordance with some embodiments.

FIG. 10 is an example of a process 1000 for determining image data based on optical signals detected by an optical detector. For ease of description, the process 1000 is described below as being performed by the FPGA 155 of the FD-DOS device 100 illustrated in FIG. 1. At block 1005, the FPGA 155 captures digital sample data for the detected optical signals. At block 1010, the FPGA 155 performs a Fourier transform (for example, a single frequency discrete Fourier transform (DFT), a full fast Fourier transform (FFT) and/or a Goertzel algorithm) on the digital sample data to determine measured amplitudes. At block 1015, the FPGA 155 transforms the measured amplitudes based on a responsivity curve of the optical sensor. At block 1020, the FPGA 155 transforms the measured amplitudes into input amplitudes based on a responsivity curve of the diode. At block 1025, the FPGA 155 determines calibration coefficients based on calibration phantom measurements. For example, in some embodiments, prior to process 1000, a calibration measurement on a phantom with known optical properties is taken using, for example, method 500 and transferred to a memory in the FPGA 155. In some embodiments, the FPGA 155 determines the calibration coefficients in about 3 to 8 clock cycles. At block 1030, the FPGA 155 determines corrected phase data and amplitude data based on calibrated measured data. At block 1035, the FPGA 155 loads a forward modeled lookup table in a memory. For example, the FPGA 155 loads a forward modeled lookup table into a fast searchable hardware RAM included in the FPGA 155 or in the memory 160. At block 1040, the FPGA 155 determines calibrated scattering data and absorption data from the forward modeled lookup table. At block 1045, the FPGA 155 determines chromophore concentrations (for example, deoxy/Oxy-hemoglobin (Hb, HHb), water, and lipid concentrations) based on the calibrated scattering data, the calibrated absorption data, and predetermined molar extinction coefficients. At block 1050, the FPGA 155 determines a bi-cubic interpolated image based on the chromophore concentrations. In some embodiments, the FPGA 155 performs the process 1000 in less than one second. In some embodiments, each subsequent scan uses the calibration data to correct amplitude and phase accounting for system dependent response. In some embodiments, during sample capture, the residuals of measured phase and amplitude are determined in parallel in order to find the optical properties associated with the lowest residuals.

Figure 11A:
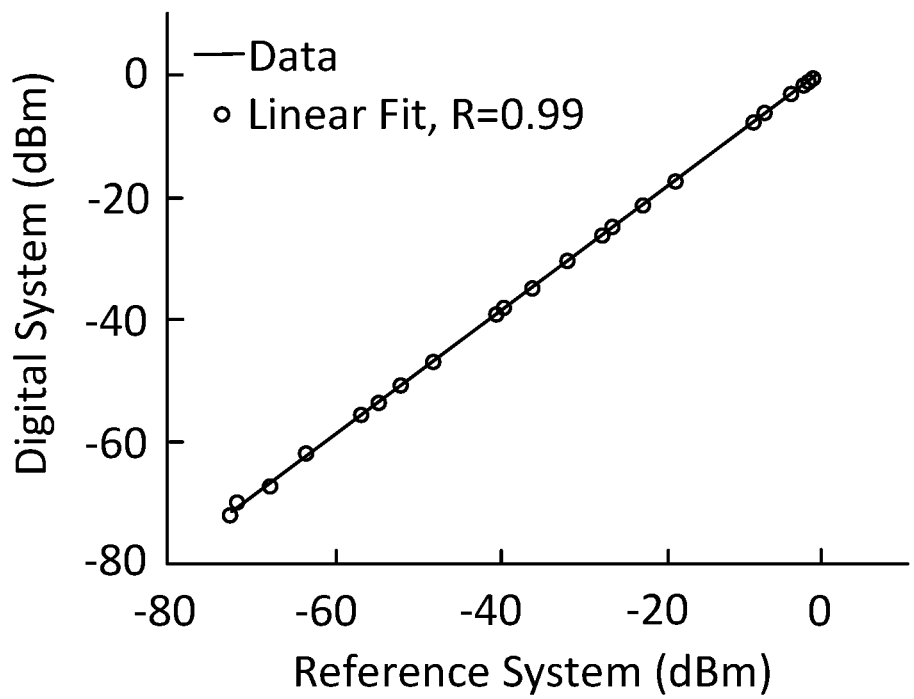
FIG. 11A is a graph of an example amplitude linearity from a noise floor to −1.5 dBM.
Figure 11B:
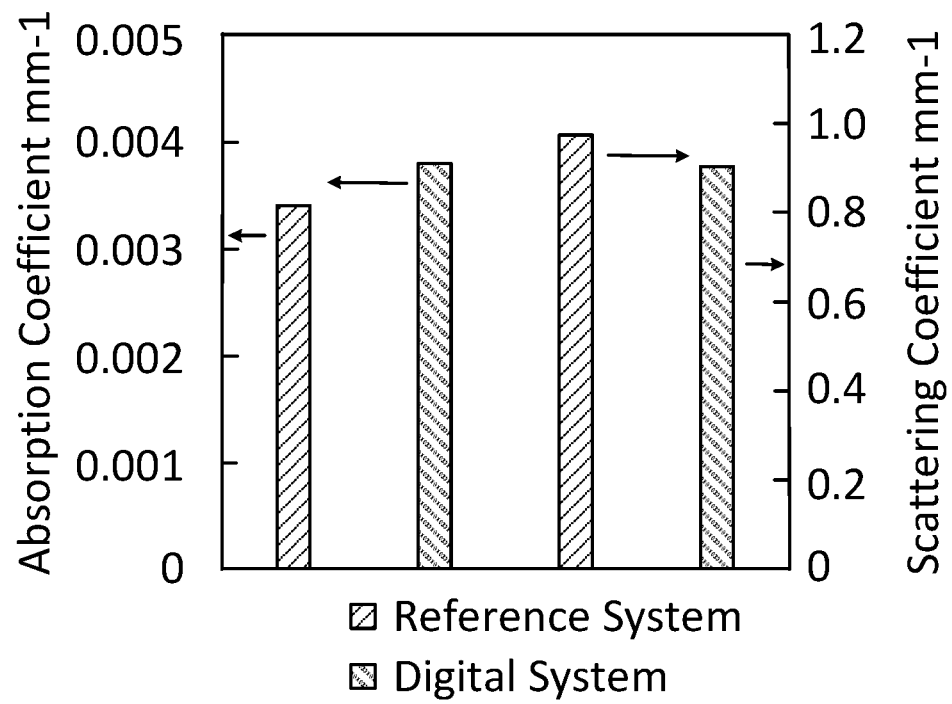
FIG. 11B is a graph of an example optical property recovery of a digital DOS system and a reference system.

Instrument validation can be performed by comparing a reference system to a custom all-digital based DOS system. For example, validation can be performed by: 1) assessing signal to noise, linearity, and dynamic range to optical signals, and 2) comparing recovered optical properties of tissue-simulating phantoms. As illustrated in FIG. 11A, the digital system response is within 3% of the reference system with a similar noise floor of −72 dBm. In one example, optical properties measured with the digital system were within 12% for absorption and 7% for scattering as compared to the reference, as illustrated in FIG. 11B.

Figure 12B:
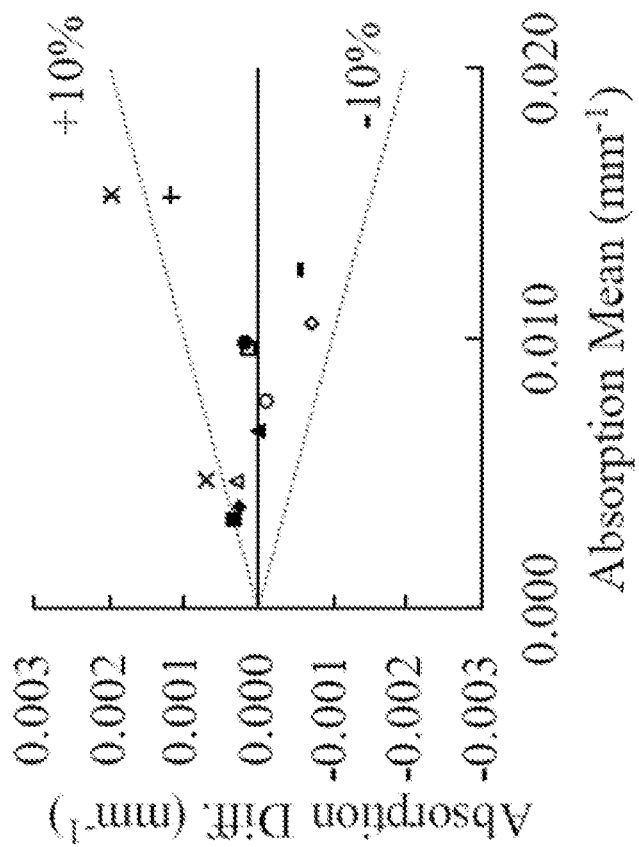
FIG. 12B is a graph of an example Bland-Altman comparison of scattering coefficients recovered with a silicon photomultiplier and an avalanche photodiode.
Figure 12A:
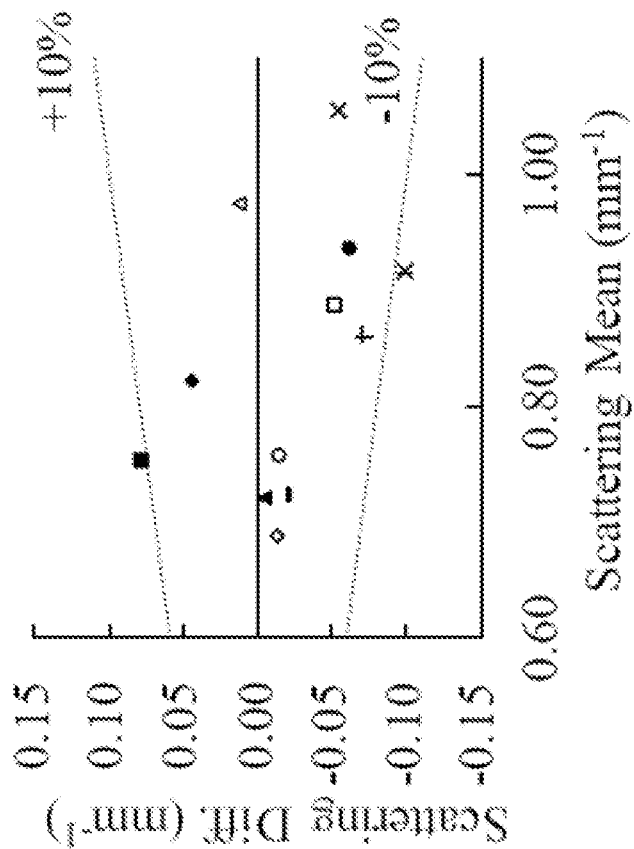
FIG. 12A is a graph of an example Bland-Altman comparison of absorption coefficients recovered with a silicon photomultiplier and an avalanche photodiode.

The optical properties of different silicone-based tissue simulating phantoms can be separately measured using the SiPM and the APD described above in Table 1. For example, the radiofrequency outputs of the photodetectors can be directly connected to an FD-DOS module which contains excitation wavelengths of 659 nanometers, 687 nanometers, 786 nanometers, and 829 nanometers. The SiPM can be biased at 33 volts for a gain of 1.5e6 and used without any form of amplification. On the other hand, the APD can be incorporated into a pre-amplification module (for example, a C5658 module with S12060-10 APD from Hamamatsu Photonics) and be biased for an intrinsic APD gain of 100. The APD module adds about another 40 decibels (RF power gain), for a total system gain of 10,000. Both photodetector can be placed directly on the phantom surface, requiring no fiber coupling. The optical property recoveries at a fixed source/detector separation of 28 millimeters can be compared in Bland-Altman format. For example, FIGS. 12A and 12B are graphs of an example Bland-Altman comparison of absorption coefficients and reduced scattering coefficients recovered with the SiPM and the APD for three different phantoms. The x's in FIGS. 12A and 12B represent data for a first phantom excited with a wavelength of 659 nanometers. The triangles in FIGS. 12A and 12B represent data for the first phantom excited with a wavelength of 687 nanometers. The filled diamonds in FIGS. 12A and 12B represent data for the first phantom excited with a wavelength of 786 nanometers. The filled squares in FIGS. 12A and 12B represent data for the first phantom excited with a wavelength of 829 nanometers. The filled circles in FIGS. 12A and 12B represent data for a second phantom excited with a wavelength of 659 nanometers. The non-filled squares in FIGS. 12A and 12B represent data for the second phantom excited with a wavelength of 687 nanometers. The non-filled circles in FIGS. 12A and 12B represent data for the second phantom excited with a wavelength of 786 nanometers. The filled triangles in FIGS. 12A and 12B represent data for the second phantom excited with a wavelength of 829 nanometers. The xI's in FIGS. 12A and 12B represent data for a third phantom excited with a wavelength of 659 nanometers. The plus signs in FIGS. 12A and 12B represent data for the third phantom excited with a wavelength of 687 nanometers. The minus signs in FIGS. 12A and 12B represent data for the third phantom excited with a wavelength of 786 nanometers. The diamonds in FIGS. 12A and 12B represent data for the third phantom excited with a wavelength of 829 nanometers.

Figure 13A:
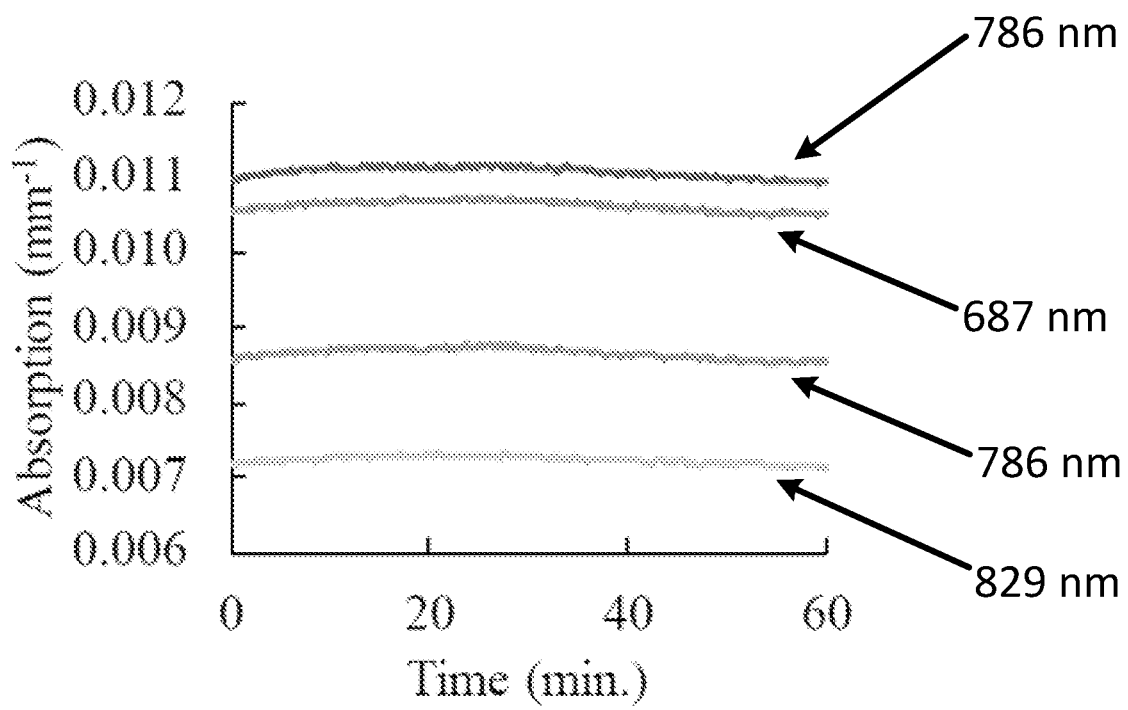
FIG. 13A is a graph of example drift in recovered absorption coefficients over an hour long period on a single tissue simulating phantom at four wavelengths with a silicon photomultiplier.
Figure 13B:
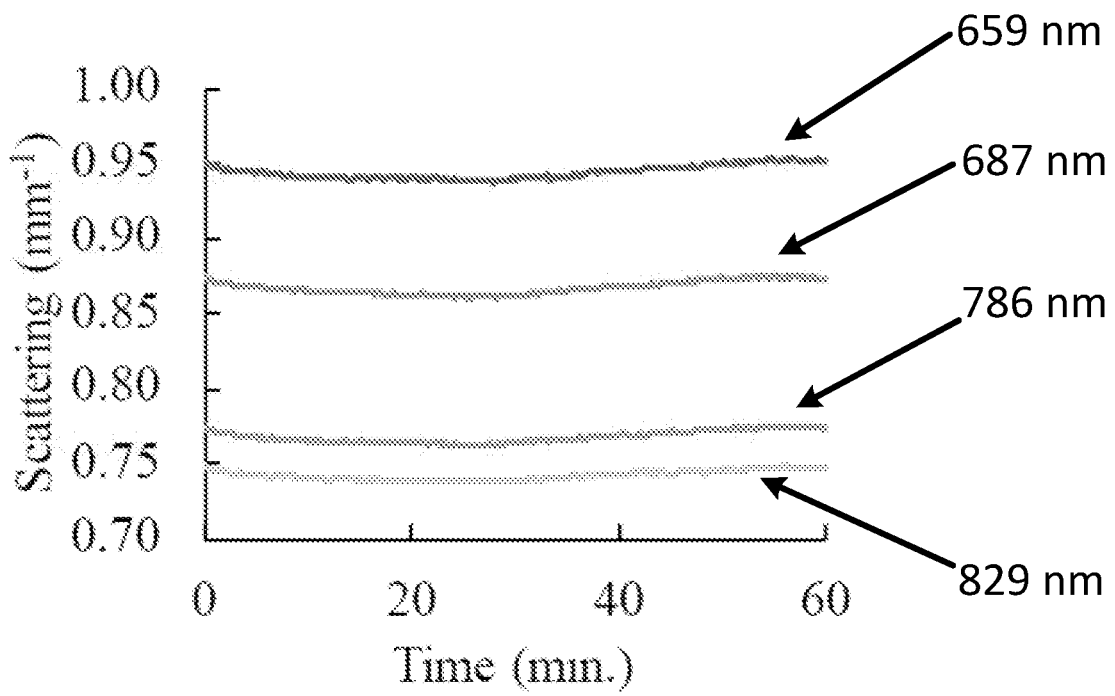
FIG. 13B is a graph of example drift in recovered scattering coefficients over an hour long period on a single tissue simulating phantom at four wavelengths with a silicon photomultiplier.

The precision and stability of FD-DOS with an SiPM can be characterized by repeatedly measuring the optical properties of a tissue-simulating phantom a period of time. For example, the precision and stability of FD-DOS with an SiPM can be characterized by repeatedly measuring (every 15 seconds) the optical properties of a tissue-simulating phantom for one hour (see FIGS. 13A and 13B). As illustrated in FIGS. 13A and 13B, a coefficient of variation is less than 1% in optical properties at all four wavelengths. The optical property recoveries illustrated in FIGS. 13A and 13B do show slowly varying drift, which is due to the temperature dependence of the SiPM gain.

Figure 14A:
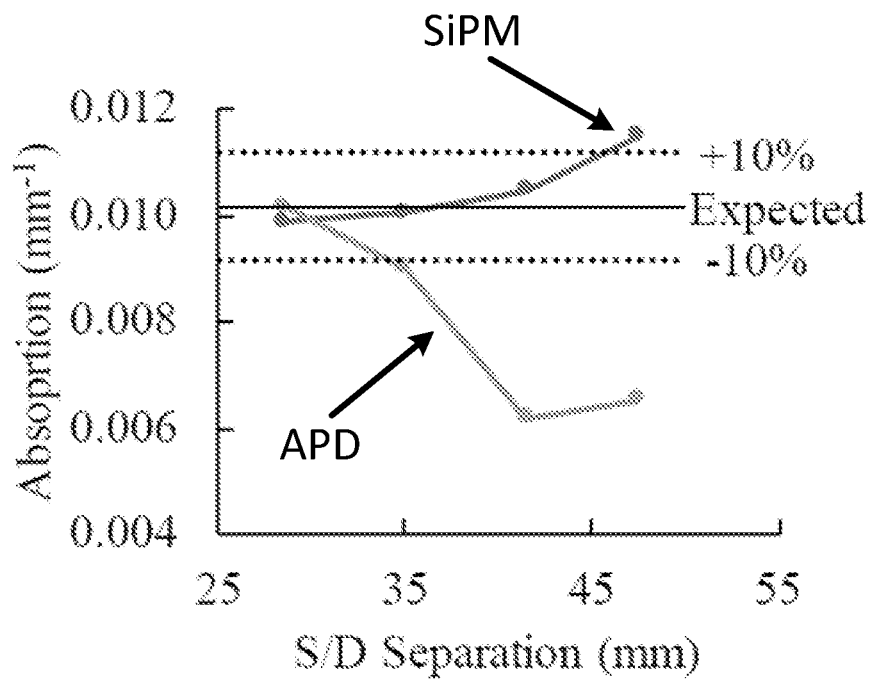
FIG. 14A is a graph of example absorption optical property recoveries on a tissue-simulating phantom at a wavelength of 659 nanometers for multiple source/detector separations for a silicon photomultiplier and an avalanche photodiode.
Figure 14B:
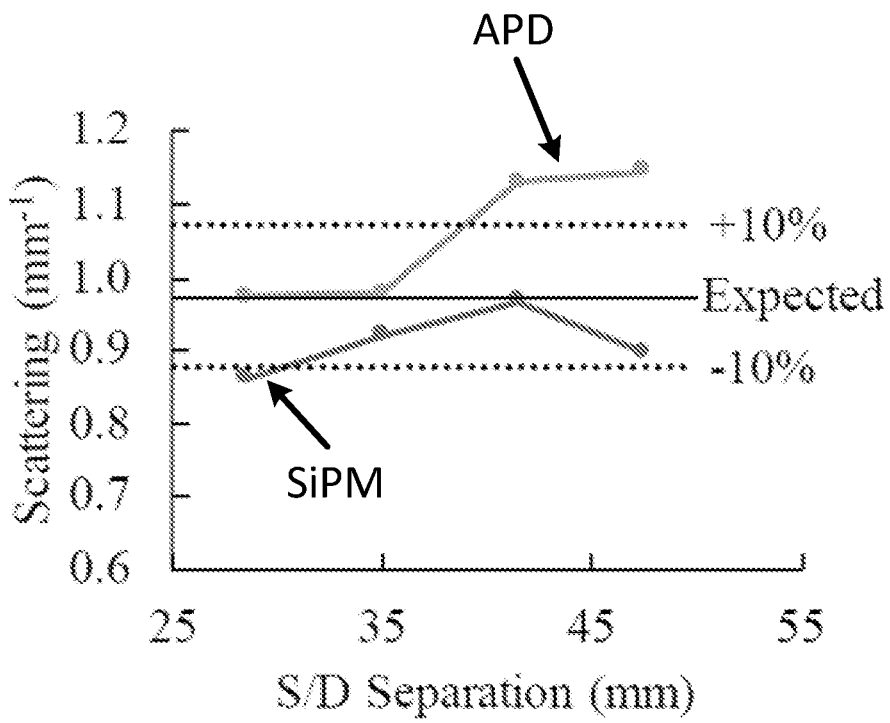
FIG. 14B is a graph of example reduced scattering optical property recoveries on a tissue-simulating phantom at a wavelength of 659 nanometers for multiple source/detector separations for a silicon photomultiplier and an avalanche photodiode.
Figure 14C:
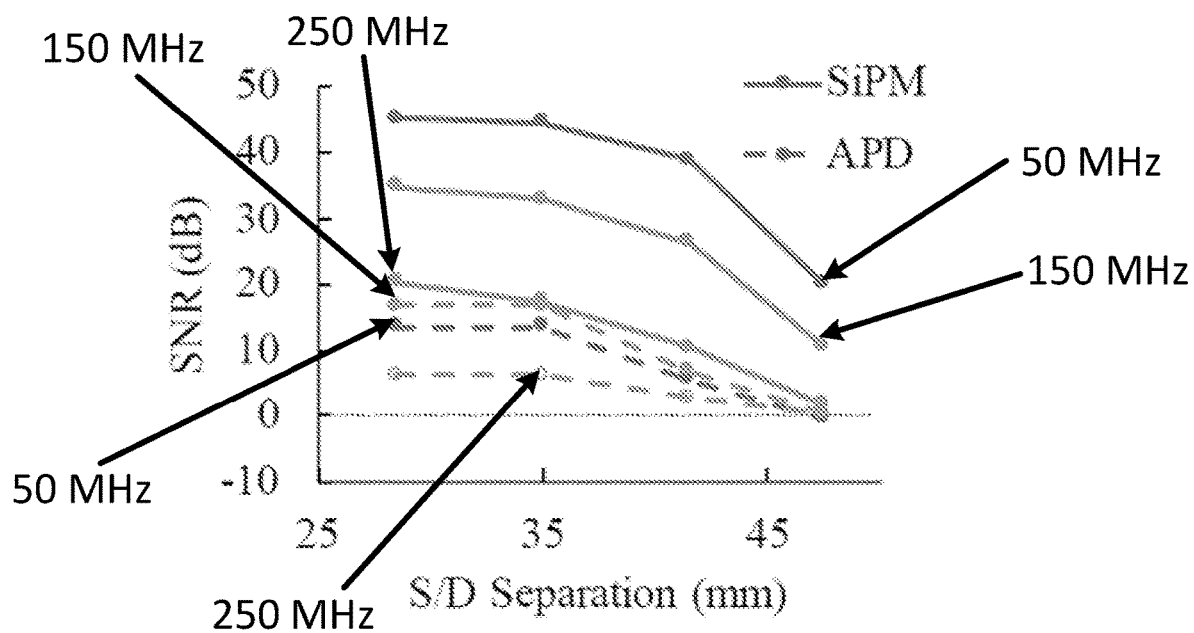
FIG. 14C is a graph of example signal to noise ratios as a function of source/detector separation for a silicon photomultiplier and an avalanche photodiode at three different frequencies.
Figure 14D:
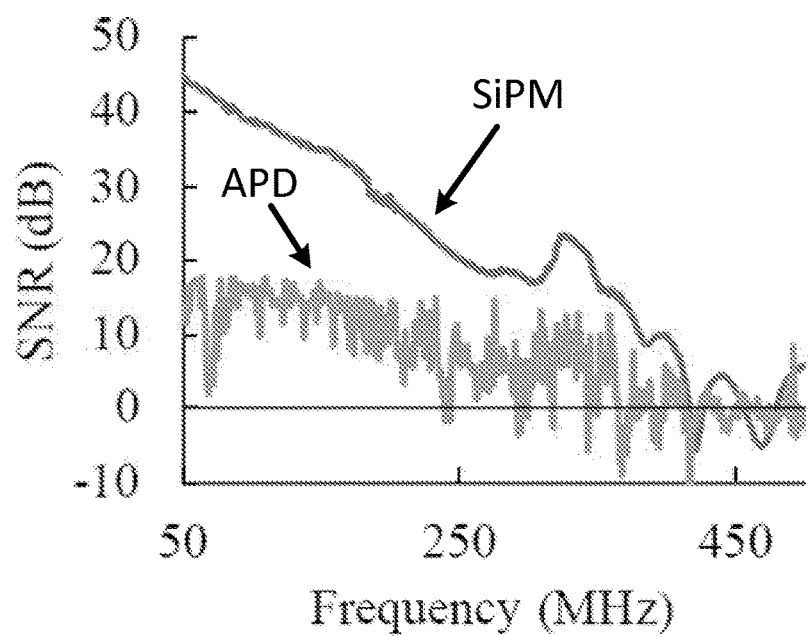
FIG. 14D is a graph of example signal to noise ratios as a function of frequency for a silicon photomultiplier and an avalanche photodiode at a 28 millimeter source/detector separation.

The single-wavelength optical property recoveries of an SiPM-based system and an APD-based system can be compared on a silicon-based homogeneous tissue-simulating phantom while varying the source/detector separations. For example, FIGS. 14A and 14B are graphs of example absorption and reduced scattering optical property recoveries on a 50 millimeter thick silicone-based homogeneous tissue-simulating phantom at a wavelength of 659 nanometers with source/detectors separations of 28 millimeters, 35 millimeters, 42 millimeters, and 48 millimeters. As illustrated in FIGS. 14A and 14B, the APD-based system recovers optical properties at 35 millimeters within 10% of the expected value at the shortest 28 millimeter source/detector separation. Also, as illustrated in FIGS. 14A and 14B, the APD-based system optical property recoveries at longer source/detector separations diverge rapidly from the expected value with errors greatly exceeding 10%. As illustrated in FIGS. 14A and 14B, the SiPM-based system recovers optical properties within 13% (10% for most optical properties) of the APD-based system's 28 millimeter source/detector values for all measured source/detector separations. Examples of the signal to noise ratio as a function of source/detector separation for both photodiodes on the phantom at excitation frequencies of 50 megahertz, 150 megahertz, and 250 megahertz are illustrated in FIGS. 14C and 14D. As illustrated in FIGS. 14C and 14D, the signal to noise ratio for the SiPM-based system is about 5 to 30 decibels higher than the APD-based system at all source/detector separations and at frequencies up to about 400 megahertz.

One or more embodiments are described and illustrated in the description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

What is claimed is:

1. A frequency domain diffuse optical spectroscopy device, comprising:
   a housing sized to be handheld, wherein a light source is positioned at a first end of the housing;
   a radio frequency signal generator;
   a driver coupled to the radio frequency signal generator;
   the light source coupled to the driver and configured to generate modulated light at a plurality of different wavelengths and a plurality of different modulation frequencies, the light source for emitting the modulated light at a sample;
   a silicon photomultiplier configured to generate analog detection signals indicative of amplitude and phase of radio frequency modulation components of detected optical signals emanating from the sample in response to the modulated light;
   an analog to digital conversion circuit (ADC) coupled to the radio frequency signal generator and coupled to the silicon photomultiplier, wherein the ADC is configured to generate digital sample values from the analog detection signals; and
   an electronic processing circuit (EPC) coupled to the analog to digital conversion circuit and configured to
      determine absorption values and scattering values based on the digital sample values,
      determine concentration values based on the absorption values and the scattering values, and
      determine an image stream based on the concentration values.

2. The frequency domain diffuse optical spectroscopy device of claim 1, wherein the EPC is further configured to determine first amplitude data and phase data from the digital sample values, adjust the first amplitude data based on an inverse response of the silicon photomultiplier to determine second amplitude data, and determine the absorption values and the scattering values based on the second amplitude data and the phase data.

3. The frequency domain diffuse optical spectroscopy device of claim 2, wherein the EPC is further configured to determine the first amplitude data and the phase data from the digital sample values using a Goertzel algorithm.

4. The frequency domain diffuse optical spectroscopy device of claim 1, further comprising one or more orientation sensors configured to generate orientation signals, wherein the EPC is further configured to correlate the orientation signals to the image stream.

5. The frequency domain diffuse optical spectroscopy device of claim 1, further comprising a communication module coupled to the EPC and configured to transmit the image stream.

6. A frequency domain diffuse optical spectroscopy system, comprising:
the frequency domain diffuse optical spectroscopy device of claim 1; and
a display device configured to receive and display the image stream.

7. The frequency domain diffuse optical spectroscopy device of claim 1, wherein the EPC is further configured such that a frame rate of the image stream is greater than thirty hertz.

8. The frequency domain diffuse optical spectroscopy device of claim 1, wherein the EPC includes a field programmable gate array.

9. The frequency domain diffuse optical spectroscopy device of claim 1, wherein the analog to digital conversion circuit is configured to undersample the analog detection signals.

10. The frequency domain diffuse optical spectroscopy device of claim 1, further comprising a battery module for power generation.

11. The frequency domain diffuse optical spectroscopy device of claim 10, wherein the radio frequency signal generator, the driver, the silicon photomultiplier, the analog to digital conversion circuit, the EPC, and the battery module are mounted in the housing.

12. The frequency domain diffuse optical spectroscopy device of claim 1, wherein the radio frequency signal generator is configured to generate radio frequency modulation signals, and wherein the radio frequency signal generator is further configured to increase power of the radio frequency modulation signals as a function of frequency.

13. The frequency domain diffuse optical spectroscopy device of claim 1, wherein signals from the silicon photomultiplier to the ADC are not amplified, and wherein the ADC generates digital reference values from radio frequency modulation signals.

14. The frequency domain diffuse optical spectroscopy device of claim 1, wherein the driver comprises a plurality of DC bias drivers which drives the light source and modulates light at a plurality of different wavelengths and a plurality of different modulation frequencies.

15. The frequency domain diffuse optical spectroscopy device of claim 14, wherein the light source comprises multiple laser diodes each configured to emit at a different wavelength, wherein each of the multiple laser diodes are coupled to a separate DC bias driver of the plurality of DC bias drivers.

16. The frequency domain diffuse optical spectroscopy device of claim 1, wherein the EPC comprises a field programmable gate array and a memory, and wherein the EPC is configured to receive digital sample values and digital references values from the ADC.

17. The frequency domain diffuse optical spectroscopy device of claim 1, wherein the EPC is further configured to:
process digital sample values into a frequency domain representation using a Fourier transform.

18. The frequency domain diffuse optical spectroscopy device of claim 17, wherein the EPC uses a full fast Fourier transform (FFT) to determine the amplitude and phase responses from the digital sample values.

19. The frequency domain diffuse optical spectroscopy device of claim 17, wherein the EPC uses a Goertzel algorithm to determine the amplitude and phase responses from the digital sample values faster than with a full FFT.

* * * * *